(12) United States Patent
Nezu et al.

(10) Patent No.: US 8,748,128 B2
(45) Date of Patent: Jun. 10, 2014

(54) TRANSPORTER GENES OATP-B, C, D, AND E

(75) Inventors: Jun-Ichi Nezu, Ibaraki (JP); Asuka Ose, Ibaraki (JP); Akira Tsuji, Ishikawa (JP)

(73) Assignees: Chugai Seiyaku Kabushiki Kaisha, Tokyo (JP); Akira Tsuji, Ishikawa (JP)

( * ) Notice: Subject to any disclaimer, the term of this patent is extended or adjusted under 35 U.S.C. 154(b) by 0 days.

(21) Appl. No.: 12/759,605

(22) Filed: Apr. 13, 2010

(65) Prior Publication Data

US 2010/0196960 A1 Aug. 5, 2010

Related U.S. Application Data

(60) Division of application No. 11/337,061, filed on Jan. 19, 2006, now abandoned, which is a division of application No. 10/101,921, filed on Mar. 20, 2002, now Pat. No. 7,045,316, which is a continuation-in-part of application No. PCT/JP00/06416, filed on Sep. 20, 2000.

(30) Foreign Application Priority Data

Sep. 21, 1999 (JP) .................................... 11/267835

(51) Int. Cl.
*C12P 21/00* (2006.01)

(52) U.S. Cl.
USPC ...................................... 435/69.1; 435/320.1

(58) Field of Classification Search
None
See application file for complete search history.

(56) References Cited

U.S. PATENT DOCUMENTS

| | | | | |
|---|---|---|---|---|
| 4,316,962 | A * | 2/1982 | Viza | 435/372 |
| 7,795,392 | B2 * | 9/2010 | Kirchgessner et al. | 530/350 |
| 2003/0022286 | A1 | 1/2003 | Curtis | |

FOREIGN PATENT DOCUMENTS

| | | |
|---|---|---|
| EP | 1 186 672 A2 | 3/2002 |
| EP | 1 186 682 A2 | 3/2002 |
| EP | 1 223 217 | 7/2002 |
| JP | 2000/116384 A | 4/2000 |
| JP | 2001/046083 A | 2/2001 |
| WO | WO 96/27009 | 9/1996 |
| WO | WO 98/42738 | 10/1998 |
| WO | WO 99/19339 | 4/1999 |
| WO | WO 00/01817 | 1/2000 |
| WO | WO 00/08157 | 2/2000 |
| WO | WO 00/09557 | 2/2000 |
| WO | WO 01/09185 | 2/2000 |
| WO | WO 00/26245 | 5/2000 |
| WO | WO 00/29574 | 5/2000 |
| WO | WO 00/55173 | 9/2000 |
| WO | WO 00/61755 | 10/2000 |
| WO | WO 00/71566 | 11/2000 |
| WO | WO 01/74897 | 10/2001 |

OTHER PUBLICATIONS

Bisson, et al, 1993, Crit Rev Biochem Mol Biol, 28:259-308.*
Liang, H., et al, 1998, Mol. Cell. Biol. 18(2): 926-935.*
Naef et al. Physical Review E, vol. 65, Apr. 9, 2002.*
Abe et al., "Identification of a Novel Gene Family Encoding Human Liver-specific Organic Anion Transporter LST-1," *J. Biol. Chem.* 274(24):17159-17163, (1999).
Abe et al., "Molecular Characterization and Tissue Distribution of a New Organic Anion Transporter Subtype (oatp3) That Transports Thyroid Hormones and Taurocholate and Comparison with oatp2," *J. Biol. Chem.* 273(35):22395-22401 (1998).
Abe et al., EMBL Accession No. AF060500, (Jun. 15, 1999).
Abe et al., EMBL Accession No. Q9Y6L6, (Oct. 16, 2001).
Bisson, et al., "Yeast sugar transporters," *Crit. Rev. Biochem. Mol. Biol.* 28:259-308 (1993).
Campbell et al., *Theriology* 47(1):63-72 (1997).
EMBL Accession No. AA280224, "zt04c07.r1 NCI_CGAP_GCB1 *Homo sapiens* cDNA clone IMAGE:712140 5' similar to SW:OATP_Human P46721 Sodium-Independent Organic Anion Transporter ; mRNA sequence," (Apr. 3, 1997).
EMBL Accession No. AB031050, "*Homo sapiens* mRNA for organic anion transporter OATP-D, complete cds," (Jan. 11, 2000).
EMBL Accession No. AF205074, "*Homo sapiens* organic anion transporter polypeptide-related protein 3 (OATPRP3) mRNA, complete cds," (Dec. 25, 2000).
EMBL Accession No. BE747478, "601574232F1 NIH_MGC_9 *Homo sapiens* cDNA clone IMAGE:3835614 5', mRNA sequence," (Sep. 20, 2000).
EMBL Accession No. BF308267, "601890328F1 NIH_MGC_17 *Homo sapiens* cDNA clone IMAGE:4131487 5', mRNA sequence," (Nov. 23, 2000).
Fei et al., "Expression cloning of a mammalian prot0n-coupled oligopeptide transporter," *Nature* 368:563-566 (1994).
Hsaing et al., "A Novel Human Hepatic Organic Anion Transporting Polypeptide (OATP2)," *J. Biol. Chem.* 274(52):37161-37168 (1999).
Hsiang et al., EMBL Accession No. AF205071, (Dec. 28, 1999).
International Search Report from the prior PCT Application No. PCT Application No. PCT/JP00/06416, 4 pages, (mailed on Dec. 26, 2000).

(Continued)

*Primary Examiner* — Brian J Gangle
*Assistant Examiner* — Andrea McCollum
(74) *Attorney, Agent, or Firm* — Klarquist Sparkman, LLP

(57) ABSTRACT

Four novel transporter genes were successfully cloned by screening novel transporter genes based on the human OATP transporter gene sequence. These transporters are useful in the development of drugs by taking advantage of the activity of transporting biological substances and various drugs. It was also found that these transporter genes have single nucleotide polymorphisms (SNP). Gene diagnosis based on the polymorphisms (such as SNP) in these transporter genes enables one to judge, for example, the efficacy of a drug therapy.

10 Claims, 6 Drawing Sheets

(56) References Cited

OTHER PUBLICATIONS

Jacquemin et al., "Expression cloning of a rat liver Na+-independent organic anion transporter," *Proc. Natl. Acad. Sci.*, 91(1):133-137, (Jan. 1994).
Kanai et al., "Identification and Characterization of a Prostaglandin Transporter," *Science* 268:866-869 (1995).
Kaufman et al., "Transgenic analysis of a 100-kb human beta-globin cluster-containing DNA fragment propagated as a bacterial artificial chromosome," *Blood* 94:3178-3184 (1999).
Koenig et al., EMBL Accession No. AJ132573, (Dec. 10, 1999).
Konig et al., "Localization and genomic organization of a new hepatocellular organic anion transporting polypeptide," *The Journal of Biological Chemistry* 275(30):23161-23168, 2000.
Konig et al., *Am. J. Physiol. Gastrointest. Liver Physiol.* 278(1):G156-G164, (2000).
Kullak-Ublick et al., "Molecular and Functional Characterization of an Organic Anion Transporting Polypeptide Cloned from Human Liver," *Gastroenterology* 109(4):1274-1285 (1995).
Liang, H., et al., "Trinucleotide insertions, deletions, and point mutations in glucose transporters confer K+ uptake in *Saccharomyces cerevisiae*," *Mol. Cell. Biol.* 18(2):926-935 (1998).
Meier et al., "Substrate Specificity of Sinusoidal Bile Acid and Organic Anion Uptake Systems in Rat and Human Liver," *Hepatology* 26(6):1667-1677 (Dec. 1997).
Nagase et al., "Prediction of the coding sequences of unidentified human genes. XII. The complete sequences of 100 new cDNA clones from brain which code for large proteins in vitro," *DNA Research* 5(6):355-364 (1998).
Nagase et al., Genbank Accessoin No. AB020687, 094956 (1998).
National Cancer Institute, EMBL Accession No. AI734250, (Jun. 18, 1999).
Nezu et al., EMBL Accession No. AB026257, (Jun. 8, 1999).
Nezu et al., EMBL Accession No. AL117465, (May 30, 2000).
Phillips, A., *Pharmacology* 53:1169-1174 (2001).
Sekine et al., "The multispecific organic anion transporter (OAT) family," *Pflügers Arch—Eur J Physiol*, 440:337-350 (2000).
Strausberg, et al, EMBL Accession No. AI052501, (Sep. 16, 1998).
Strausberg, et al., EMBL Accession No. AI668650, (May 17, 1999).
Strausberg, et al., EMBL Accession No. AW138790, (Nov. 2, 1999).
Strausberg, et al., EMBL Accession No. AW590751, (Mar. 23, 2000).
Tamai et al., "Molecular Identification and Characterization of Novel Members of the Human Organic Anion Transporter (OATP) Family," *Biochem. Biophys. Res. Commun.* 273(1):251-260, (2000).
Tiorna et al., "Polymorphisms in OATP—Identification of Multiple Allelic Variants Associated with Altered Transport Activity Among European- and African-Americans," 276(38):35669-35675 (2001).
Wang et al., "Rapid analysis of gene expression (RAGE) facilitates universal expression profiling," *Nuc. Acids Res.* 27:4609-4618 (1999).
Wigley et al., "Site-specific transgene insertion: an approach*Reprod. Fert. Dev.*" 6:585-588 (1994).
Abe et al., "Identification of a Novel Gene Family Encoding Human Liver-Specific Organic Anion Transporter LST-1," *Journal of Biological Chemistry*, 274(24): 17159-17163, 1999.
Abe et al., "Molecular Characterization and Tissue Distribution of a New Organicanion Transporter Subtype (OATP3) That Transports Thyroid Hormones and Taurocholate and Comparison with OATP2," *Journal of Biological Chemistry*, 273(35): 22395-22401, 1998.
Kanai et al., "Identification and Characterization of a Prostaglandin Transporter," *Science*, 268: 866-869, 1995.
Kullak-Ublick et al, "Molecular and Functional Characterization of an Organic Anion Transporting Polypeptide Cloned from Human Liver," *Gastroenterology*, 109: 1274-1282, 1995.
Meier et al., "Substrate Specificity of Sinusoidal Bile Acid and Organic Anion Uptake Systems in Rat and Human Liver," *Hepatology*, 26(6): 1667-1677, 1997.
Noé et al., "Isolation of a Multispecific Organic Anion and Cardiac Glycoside Transporter from Rat Brain," *PNAS U.S.A.*, 94(19): 10346-10350, 1997.
Nozawa et al., "Functional Characterization of pH-Sensitive Organic Anion Transporting Polypeptide OATP-B in Human," *J. Pharmacol. Exp. Ther.*, 308(2): 438-445, 2003.
Tamai et al., "Functional Characterization of Human Organic Anion Transporting Polypeptide B (OATP-B) in Comparison with Liver-Specific OATP-C," *Pharm. Res.*, 18(9): 1262-1269, 2001.
Tamai et al., "Molecular Identification and Characterization of Novel Members of the Human Organic Anion Transporter (OATP) Family," *Biochem. Biophys. Res. Commun.*, 273(1): 251-260, 2000.
EMBL Accession No. AI022939, 1999, 1 page.
EMBL Accession No. W96330, 1999, 2 pages.
NCBI GenBank Accession No. AB026256, "Human Organic Anion Transporter OATP-B," 2 pages (Jun. 8, 1999).

\* cited by examiner

TRANSPORTER GENES OATP-B, C, D, AND E

CROSS RELATED REFERENCE TO PRIOR APPLICATIONS

This is a divisional of U.S. patent application Ser. No. 11/337,061, filed Jan. 19, 2006 now abandoned, which is a divisional of U.S. patent application Ser. No. 10/101,921, filed Mar. 20, 2002, now issued as U.S. Pat. No. 7,045,316, which are all incorporated by reference herein. U.S. patent application Ser. No. 10/101,921 is a continuation-in-part of International Application No. PCT/JP00/06416, filed Sep. 20, 2000, which claims priority to Japanese Patent Application No. 11/267835, filed Sep. 21, 1999.

TECHNICAL FIELD

The present invention relates to transporter families, proteins involved in the transport of substances from the outside to the inside of cells and vice versa.

BACKGROUND ART

Recently, the involvement of various transporters localized on the plasma membrane in the uptake system for nutrients and endogenous substances into cells and their transport mechanisms have been clarified (Tsuji, A. and Tamai, I., Pharm. Res., 13, 963-977, 1996). These transporters recognize the structures of substances to be transported to selectively transport specific substances across biological membranes. Transporters that recognize structures of a relatively wide range may possibly recognize foreign substances, such as drugs, by mistake, and actively take in them into cells. It is believed that drugs permeate through the plasma membrane fundamentally by simple diffusion, depending on their physicochemical properties such as molecular size, fat-solubility, and hydrogen-binding capacity. Particularly, according to the pH partition hypothesis, in the case of ionic drugs, only molecules in the non-dissociated form can permeate through the plasma membrane. However, it has become evident that a number of drugs penetrate through the cell membrane by a specific mechanism other than simple diffusion, that is, an active transport mediated by transporters, particularly in organs that require efficient exchange of intracellular and extracellular substances, including small intestine, uriniferous tubule, placenta, epithelial cells of choroid plexus, hepatocytes, and blood-brain barrier (Tamai, I. and Tsuji, A., Pharmacia, 31, 493-497, 1995; Saito, H. and Inui, K., Igaku no Ayumi, 179, 393-397, 1996; Tamai, I., Yakubutsu Dotai (Pharmacokinetics), 11, 642-650, 1996). For example, it is known that although oral β-lactam antibiotics of the non-esterified type are amphoteric or negatively charged in physiological pHs and sparingly soluble in fat, they are readily absorbed through the intestine. A transport study using the isolated membrane-vesicles system demonstrated that an $H^+$-driven peptide transporter localized on the brush-border membrane is involved in the absorption process of these drugs (Okano, T. et al., J. Biol. Chem. 261, 14130-14134, 1986). Although the specificity of a peptide transport system in terms of the peptide size is so strict as to recognize di- or tri-peptides but not tetrapeptides or larger peptides, it has a rather broad substrate specificity so as to recognize peptides comprising non-natural amino acids. The peptide transporter mistakenly mediates transport of β-lactam antibiotics due to its broad substrate specificity. This property has been unexpectedly utilized in the clinical field (Tsuji, A., American Chemical Society (eds. Taylor, M. D., Amidon, G. L.), Washington, D.C., 101-134, 1995). Furthermore, it has been reported that a transporter is possibly also involved in permeation of substances with a high fat-solubility such as fatty acids through the plasma membrane (Schaffer, J. and Lodish, H., Cell, 79, 427-436, 1994).

Since various transporters are presumed to be distributed in organs and cells based on the physiological roles of the organs and cells, their distribution and functions may be specific to organs. Therefore, transporters are expected to be used to impart an organ specificity to pharmacokinetics. In other words, an organ-specific drug delivery system (DDS) can be constructed utilizing transporters. If drug absorption that relies solely on simple diffusion is improved by elevating its fat-solubility, the effect of the drug obtained in the initial transport in the liver can be enhanced and the drug can non-specifically translocate into any organ. In addition, it would also be possible to increase the drug absorption independently of its fat-solubility by designing the drug based on the substrate specificity of transporters (Hayashi, K. et al., Drug Delivery System, 11, 205-213, 1996). For this purpose, it is necessary to identify various transporters at the molecular level and analyze their properties in detail. However, molecular level identification is greatly behind studies on membrane physiology because the transporters are difficult to handle biochemically and require complicated processes in their functional assays.

Recently, cDNAs of several transporters have been cloned by the expression cloning method using *Xenopus* oocytes, a foreign gene expression system, and the structural homology among them has been revealed (Fei, Y.-J. et al., Nature, 368, 563-566, 1994). For example, Koepsell et al. cloned an organic cation transporter, OCT1, which is presumed to be localized on a basement membrane, using the expression cloning method in 1994 (Grundemann, D. et al., Nature, 372, 549-552, 1994). Subsequently, OCT2 was identified by homology cloning based on the sequence of OCT1 (Okuda, M. et al., Biochem. Biophys. Res. Commun., 224, 500-507, 1996). OCT1 and OCT2 show homology as high as 67% to each other (Grundemann, D. et al., J. Biol. Chem., 272, 10408-10413, 1997). Both of them are intensely expressed in the kidney, but differ in the organ distribution; OCT1 is also expressed in the liver, colon, and small intestine, while OCT2 expression is specific to the kidney.

In addition, another transporter, the human organic anion transporting polypeptide (OATP) transporter (hereinafter, referred to as "OATP-A"; Gastroenterology 109 (4), 1274-1282 (1995)), has been reported. This transporter is a protein capable of transporting various endogenous and foreign substances in a sodium ion-independent manner. Known substances transported by OATP-A include bromosulfophthalein, bile acids, steroid hormones, etc. Since PGT, a transporter capable of transporting prostaglandins, also shows significant homology to OATP-A, genes encoding these transporters are thought to form a gene family (the OATP family).

Only a few reports are available on identifications of transporters at the molecular level, including above reports, and it is believed that many unidentified transporters exist that can be clinically useful.

SUMMARY OF THE INVENTION

It is an object of this invention to provide novel transporter genes belonging to the OATP family, proteins encoded by these genes, and use of the genes and proteins.

DETAILED DESCRIPTION OF SEVERAL EMBODIMENTS

In order to find genes encoding novel transporters, the present inventors performed a tBLASTn search of the human EST (Expressed Sequence Tag) database (URL: http://www.ncbi.nlm.nih.gov/blast/blast.cgi) in NCBI (National Center for Biotechnology Information in U.S.A., URL: http://www.ncbi.nlm.nih.gov/index.html) with the protein sequence of human OATP transporter (Gastroenterology 109 (4), 1274-1282 (1995)) as a query. As a result, several ESTs which may encode amino acid sequences having significant homologies with the human OATP-A protein were found. Next, further searches of the database with these EST sequences as the query revealed that all of the ESTs are derived from genes of unknown functions, with the exception of those which were clearly judged to be derived from the known human OATP-A gene and human prostaglandin transporter gene (J. Clin. Invest. 98 (5), 1142-1149 (1996)) (hereinafter, abbreviated as PGT). This finding indicated that these ESTs are derived from transporter genes which have not been identified so far. Therefore, cloning of the full-length cDNA was performed by screening cDNA libraries with these EST sequences, using PCR and plaque hybridization methods, which resulted in the successful cloning of four genes encoding four novel transporter-like proteins. Since all of the proteins encoded by these genes have significant homologies with the human OATP-A protein, the genes have been designated as OATP-B, C, D and E, respectively. Thus, the present inventors discovered that all of the ESTs found by the tBLASTn search are those derived from human OATP-A, B, C, D and E as well as human PGT gene.

As described above, it has been known that the human OATP-A is a transporter protein capable of transporting a variety of endogenous and foreign substances, including bromosulfophthalein, bile acids, steroid hormones, etc., in a sodium ion-independent manner, and that the PGT protein capable of transporting prostaglandins shows a significant homology with the OATP-A protein. These transporter genes have been thought to form a family of genes (the OATP family) potentially involved in the removal of substances unnecessary for living bodies and regulation of concentrations of a variety of substances in vivo (J. Biol. Chem., 1998 Aug. 28; 273 (35): 22395-401).

It is presumed that novel members of the OATP family found in the present invention also share similar functions to OATP-A and PGT, in the regulation of in vivo concentrations of substances essential or unnecessary to living bodies. Furthermore, the present inventors also demonstrated a capability of the OATP-C protein to transport drugs, such as β-lactam antibiotics. According to these facts, it was presumed that drugs which are originally foreign substances to living bodies may possibly be taken up into or excreted from cells in a manner mediated by the OATP family proteins. Therefore, it may be possible to control pharmacodynamics and speedily design or screen drugs with a higher absorbability by utilizing the transport specificity, such as substrate specificity, and distribution pattern in vivo of the OATP-family proteins. In particular, the present inventors discovered, by analysis using RT-PCR method, that OATP-E is highly expressed in a variety of solid cancer cells but seldom in hemocytes. Thus, anticancer agents may be obtained by constructing a screening system using the OATP-E gene to screen compounds which are specifically transported into cells mediated by the OATP-E protein. Such agents are expected to have reduced cytotoxicity to hemocytes.

In addition, if the OATP family proteins are involved in the control of pharmacodynamics of drugs in vivo, the pharmacodynamics are expected to be modified by genetic polymorphism of the proteins. It has been already known that the genetic polymorphism such as the single nucleotide polymorphism (SNP) causes differences in gene expression level and in the amino acid sequences encoded among individuals (Nat. Genet. 1999 Jul. 22 (3): 231-8; Nat Genet., 1999 Jul. 22 (3): 239-47). It is expected that the genetic polymorphism in OATP family genes causes differences in transport specificities, such as transport activity and substrate specificity, of OATP proteins among individuals, leading to individual differences in in vivo pharmacodynamics of drugs and such which are controlled by OATP family proteins. In fact, it is presumed that such differences among individuals may lead to differences in effectiveness and reactivity of particular drugs. Thus, it is postulated that examination of the polymorphism, such as SNP, in OATP family genes in detail, particularly the accumulation of information on relationship between genotype and phenotype (reactivity to drugs) of these genes, can enable the prediction of the reactivity of individuals to drugs by performing genetic diagnosis of genotype of these genes in a particular individual.

In fact, the present inventors found SNPs with the following three types of amino acid mutations in normal individuals during the cloning process of OATP family genes:

polymorphism in the 486th codon of OATP-B gene (tct:Ser or ttt:Phe), polymorphism in the 130th codon of OATP-C gene (aat: Asn or gat:Asp), and polymorphism in the 174th codon of OATP-C gene (gtg: Val or gcg:Ala).

It is presumed that additional polymorphisms, besides those described herein, exist in the OATP gene family to be related to phenotypes.

In addition, in view of such critical roles of the OATP family proteins in vivo, it is presumed that disorders exist which are caused by deficiencies in transport functions due to gene mutations of these proteins. In fact, it has been reported that the gene mutation in the OCTN2 transporter, which is one of the organic cation transporters, causes systemic carnitine deficiency (SCD) (Nat. Genet. 1999 January; 21 (1): 91-4), proving the actual existence of genetic disorders caused by the mutation of transporter genes. Genetic diagnosis based on direct examination of causative transporter genes is clinically very important for such genetic disorders caused by the mutations in the transporter genes.

Genetic diagnosis to detect polymorphisms and mutations in genes of the OATP family is made possible by the structure of the OATP family genes revealed in this invention. Specifically, genetic diagnosis can be made using genes of the OATP family themselves or synthetic oligonucleotides prepared from the nucleotide sequences thereof as the primers for PCR. In addition, it has recently become possible to more conveniently detect structures or expression levels of genes by techniques referred to as DNA chip or DNA microarray techniques (Nat. Genet. 1999 volume 21 Supplement pp 1-60; Science 1999 Jan. 1; 283 (5398): 83-7). Such methods can be also carried out using genes of the OATP family themselves or synthetic oligonucleotides prepared from nucleotide sequences thereof.

Accordingly, this invention relates to novel transporters OATP-B, C, D, and E, genes encoding these transporters, and uses thereof. More specifically, the present invention provides:

(1) a DNA encoding a protein having a transporter activity selected from the group of:
  (a) a DNA encoding a protein comprising the amino acid sequence of SEQ ID NOs: 2, 4, 6, or 8;
  (b) a DNA comprising a coding region of the nucleotide sequence of SEQ ID NOs: 1, 3, 5, or 7;
  (c) a DNA encoding a protein comprising the amino acid sequence of SEQ ID NOs: 2, 4, 6, or 8, wherein one or more amino acids have been substituted, deleted, inserted, and/or added; and
  (d) a DNA that hybridizes with the DNA consisting of the nucleotide sequence of SEQ ID NOs: 1, 3, 5, or 7;
(2) a DNA encoding a partial peptide of a protein comprising the amino acid sequence of SEQ ID NOs: 2, 4, 6, or 8;
(3) a vector into which the DNA of (1) or (2) is inserted;
(4) a transformed cell harboring the DNA of (1) or (2), or the vector of (3);
(5) a protein or a peptide encoded by the DNA of (1) or (2);
(6) a method for producing the protein or peptide of (5), comprising the steps of: culturing the transformed cell of (4), and recovering the expressed protein from said transformed cell or the culture supernatant thereof;
(7) an antibody binding to the protein of (5);
(8) a polynucleotide comprising at least 15 nucleotides that is complementary to the DNA consisting of the nucleotide sequence of SEQ ID NOs: 1, 3, 5, or 7, or the complementary strand thereof;
(9) a method of screening for a compound that is transported from the outside to the inside of a cell through the intermediary of the protein of (5), comprising the steps of:
  (a) providing a cell that expresses the protein of (5) on the cell membrane;
  (b) contacting a labeled compound with said cell;
  (c) detecting whether or not the labeled compound has been taken up into the cell; and
  (d) selecting the compound that is taken up into the cell;
(10) a method of screening for a test compound that promotes or suppresses the transporter activity of the protein of (5), comprising the steps of:
  (a) providing a cell that expresses the protein of (5) on the cell membrane;
  (b) contacting a test compound and a labeled organic compound to be transported through the intermediary of the protein of (5) with said cell;
  (c) measuring the amount of the labeled organic compound that has been taken up into said cell; and
  (d) selecting the test compound that increases or decreases the amount of the labeled organic compound taken up into said cell as compared with that observed in the absence of the test compound (control).

The nucleotide sequences of cDNAs of novel transporters isolated by the present inventors, "OATP-B", "OATP-C", "OATP-D", and "OATP-E", are set forth in SEQ ID NOs: 1, 3, 5, and 7, respectively, and the amino acid sequences of the proteins encoded by said cDNAs are set forth in SEQ ID NOs: 2, 4, 6, and 8, respectively. All of these proteins have structural similarity with the human OATP-A transporter, and all are thought to form a family (the "OATP" family).

The transporters of this invention are presumed to regulate the in vivo concentrations of substances, which are either essential or unnecessary for living bodies. It is also presumed that a variety of drugs are incorporated into cells or are excreted from cells by the OATP family proteins. Therefore, it may be possible to control the pharmacodynamics of drugs, and speedily design or screen drugs with an improved absorbability using the proteins of the OATP family.

The transporter proteins of this invention include mutants of the above-described human transporters, "OATP-B", "OATP-C", "OATP-D", and "OATP-E" protein. Herein, "mutants" are referred to as proteins that have amino acid sequences which have been mutated by substitution, deletion, addition, or insertion of amino acids from the natural "OATP-B", "OATP-C", "OATP-D", or "OATP-E" proteins of SEQ ID NOs: 2, 4, 6, or 8, and that still retain the transporter activity. Mutations of amino acids in proteins may occur artificially or naturally.

The phrase "having the transporter activity" as used herein means that a protein has the activity to transport an organic compound across membranes. Examples of organic compounds include estradiol-17β-glucuronide, estron-3-sulfate, benzyl penicillin, prostaglandin E2, and so on, but are not limited thereto.

In addition, the phrase "activity to transport" as used herein includes not only the activity to transport an organic compound from the outside to inside of cells, but also that from the inside to outside of cells. The transporter proteins of this invention include those having both of these activities and those with either one of the activities. The activity of a protein to transport an organic compound can be measured, for example, by adding a labeled organic compound to cells to detect the uptake or excretion thereof, for example, by the method described in Examples.

During the cloning process of genes of the OATP family, the present inventors found SNPs with following three types of amino acid mutations in normal individuals:
  polymorphism in the 486th codon of OATP-B gene (tct:Ser or ttt:Phe),
  polymorphism in the 130th codon of OATP-C gene (aat:Asn or gat:Asp), and
  polymorphism in the 174th codon of OATP-C gene (gtg:Val or gcg:Ala).

The transporter of this invention includes proteins having the above-described mutations, namely: a protein comprising the amino acid sequence of SEQ ID NO: 2, wherein the amino acid at position 486 is substituted with Phe; a protein comprising the amino acid sequence of SEQ ID NO: 4, wherein the amino acid at position 130 is substituted with Asp; and a protein comprising the amino acid sequence of SEQ ID NO: 4, wherein the amino acid at position 174 is substituted with Ala.

Polymorphisms other than those described above are presumed to exist for "OATP-B", "OATP-C", "OATP-D", and "OATP-E", and such polymorphisms of "OATP-B", "OATP-C", "OATP-D", and "OATP-E" are also included in this invention. These polymorphisms are presumed to affect the expression level or activity of transporters and are probably related to their phenotypes. Genetic diagnosis, wherein polymorphism and mutation of the OATP family genes are detected, is made possible by further elucidating the relationship between the genes of OATP family and their phenotypes.

Examples of methods for artificially altering amino acids well known to those skilled in the art include the site-specific mutagenesis system by PCR (GIBCO-BRL, Gaithersburg, Md.); site-specific mutagenesis using oligonucleotides (Kramer, W. and Fritz, H. J. (1987) Methods in Enzymol., 154: 350-367); the Kunkel's method (Methods Enzymol. 85, 2763-2766 (1988)); etc. There is no particular limitation in the number and site of amino acid mutations so long as the mutant proteins retain the transporter activity of this invention. The preferred number of amino acids to be substituted is typically 10 amino acid residues or less, preferably 6 or less, and more preferably 3 or less.

As for the amino acid residue to be mutated, it is preferable that the amino acid be mutated into a different amino acid that allows the properties of the amino acid side-chain to be conserved. Examples of properties of amino acid side chains include hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W) (The parenthetic letters indicate the one-letter codes of amino acids).

It is well known that a protein having deletion, addition, and/or substitution of one or more amino acid residues in its protein sequence can retain the biological activity of the original protein (Mark, D. F. et al., Proc. Natl. Acad. Sci. U.S.A. 81:5662-5666 (1984); Zoller, M. J. and Smith, M., Nucleic Acids Res. 10:6487-6500 (1982); Wang, A. et al., Science 224:1431-1433; Dalbadie-McFarland, G. et al., Proc. Natl. Acad. Sci. U.S.A. 79:6409-6413 (1982)).

An example of a protein to which plural amino acid residues are added to the amino acid sequence of human "OATP-B", "OATB-C", "OATP-D", or "OATP-E" protein (SEQ ID NOs: 2, 4, 6, or 8) is a fusion protein comprising human "OATP-B", "OATP-C", "OATP-D", or "OATP-E" protein. Fusion proteins are fusions of the human "OATP-B", "OATP-C", "OATP-D", or "OATP-E" protein and other peptides or proteins, and are included in the present invention. Fusion proteins can be made by techniques well known to a person skilled in the art, such as by linking the DNA encoding the human "OATP-B", "OATP-C", "OATP-D", or "OATP-E" protein of the invention with DNA encoding the other peptides or proteins, so that the frames match, inserting this fusion DNA into an expression vector, and expressing it in a host. There is no restriction as to the peptides or proteins fused to the protein of the present invention.

However, examples of known peptides that can be used as peptides to be fused to the protein of the present invention include: FLAG (Hopp, T. P. et al., Biotechnology (1988) 6: 1204-1210), 6×His consisting of six His (histidine) residues, 10×His, Influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, and such. Additional examples of proteins that can be fused to a protein of the present invention include GST (glutathione-S-transferase), Influenza agglutinin (HA), immunoglobulin constant region, β-galactosidase, MBP (maltose-binding protein), and such.

Fusion proteins can be prepared by fusing commercially available DNA encoding these peptides or proteins with the DNA encoding a protein of the present invention and expressing the fused DNA prepared.

In addition, the transporter proteins of the present invention include proteins having a high structural homology with the above-described human "OATP-B", "OATP-C", "OATP-D", or "OATP-E" proteins, and retaining the transporter activity. Such proteins include proteins, for example, derived from non-human mammals, which correspond to the human "OATP-B", "OATP-C", "OATP-D", or "OATP-E" proteins. A protein having a high structural homology with the human "OATP-B", "OATP-C", "OATP-D", or "OATP-E" proteins can be isolated by, for example, the hybridization technique (Sambrook, J. et al., Molecular Cloning 2nd ed., 9.47-9.58, Cold Spring Harbor Lab. press, 1989). Specifically, based on the DNA sequences (SEQ ID NOs: 1, 3, 5, or 7) encoding the above-described human "OATP-B", "OATP-C", "OATP-D", or "OATP-E" proteins or portions thereof, a DNA derived from non-human mammals having a high homology with the aforementioned DNAs can be isolated using the affinity among DNAs, and the desired protein can be prepared from the isolated DNA. Non-human mammals to be used for isolating DNAs include monkeys, mice, rats, rabbits, cattle, pigs, dogs, cats, and so on, but the invention is not limited to them.

One example of hybridization conditions (stringent conditions) for isolating such DNAs is as follows. That is, after the pre-hybridization at 55° C. for 30 min or more in the "EXPRESSHYP™ Hybridization Solution" (CLONTECH), a labeled probe is added, and hybridization is performed by heating the reaction mixture at 37° C. to 55° C. for 1 hour (h) or more. Then, the reaction product is successively washed in 2× saline sodium citrate (SSC) and 0.1% sodium dodecyl sulfate (SDS) three times at room temperature for 20 minutes (min), and then in 1×SSC and 0.1% SDS once at 37° C. for 20 min.

More preferable conditions (more stringent conditions) are as follows: After the pre-hybridization at 60° C. for 30 min or more in the "EXPRESSHYP™ Hybridization Solution" (CLONTECH), a labeled probe is added, and hybridization is performed by heating the reaction mixture at 60° C. for 1 h or more. Then, the reaction product is successively washed in 2×SSC and 0.1% SDS three times at room temperature for 20 min, and then in 1×SSC and 0.1% SDS twice at 50° C. for 20 min.

Still more preferable conditions (still more stringent conditions) are as follows: After pre-hybridization at 68° C. for 30 min or more in the "EXPRESSHYP™ Hybridization Solution" (CLONTECH), a labeled probe is added, and hybridization is performed by heating the reaction mixture at 68° C. for 1 h or more. Then, the reaction product is successively washed in 2×SSC and 0.1% SDS three times at room temperature for 20 min, and then in 0.1×SSC and 0.1% SDS twice at 50° C. for 20 min. However, several factors, such as temperature or salt concentration, can influence the stringency of hybridization and one skilled in the art can suitably select the factors to accomplish a similar stringency.

It is also possible for those skilled in the art to similarly isolate a gene having a high homology with the human "OATP-B", "OATP-C", "OATP-D", or "OATP-E" genes, and obtain desired proteins from these genes using techniques other than the hybridization technique, for example, the polymerase chain reaction.

Such proteins isolated by hybridization and polymerase chain reaction techniques are thought to have a high homology with the human "OATP-B", "OATP-C", "OATP-D", or "OATP-E" proteins. "High homology" means at least 80% or more, preferably 90% or more, and more preferably 95% or more of homology at the amino acid level. The homology of a protein can be determined by following the algorithm in "Wilbur, W. J. and Lipman, D. J., Proc. Natl. Acad. Sci. USA (1983) 80, 726-730".

A protein of the present invention may have variations in amino acid sequence, molecular weight, isoelectric point, the presence or absence of sugar chains, or form, depending on the after-mentioned cell or host used to produce it or the purification method utilized. Nevertheless, so long as the obtained protein has the transporter activity, it is within the scope of the present invention.

A protein of the present invention can be prepared as a recombinant protein or a natural protein by methods well known to those skilled in the art. A recombinant protein can be prepared by inserting a DNA (for example, the DNA comprising the nucleotide sequence of SEQ ID NOs: 1, 3, 5, or 7) encoding a protein of the present invention into an appropriate expression vector, introducing the vector into appropriate host cells, collecting the recombinant, obtaining the extract, and purifying by subjecting the extract to chromatography such as ion exchange, reverse, gel filtration, or affinity chromatography in which an antibody against a protein of the present invention is fixed on column or by combining more than one of these columns.

Also, when a protein of the present invention is expressed within host cells (for example, animal cells and E. coli) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin or factor-Xa as required.

A natural protein can be isolated by methods well known to those skilled in the art, for example, by contacting the extract of tissues or cells expressing a protein of the present invention to an affinity column in which an antibody binding to a protein of the present invention (described below) is bound so as to isolate and purify the protein from the extract. An antibody can be a polyclonal or a monoclonal antibody.

The present invention also includes a partial peptide of a protein of the present invention. A partial peptide comprising the amino acid sequence specific to the protein of the present invention comprises at least 7 amino acids, preferably 8 amino acids or more, and more preferably 9 amino acids or more. The partial peptide can be used, for example, to prepare an antibody against a protein of the present invention, to screen for a compound binding to a protein of the present invention, and to screen for accelerators or inhibitors of a protein of the present invention. Partial peptides of the proteins of the present invention include those peptides comprising the functional domains of original proteins, for example, comprising the amino acid sequence of SEQ ID NOs: 2, 4, 6, or 8. Other examples of partial peptides are those comprising one or more hydrophobic and hydrophilic regions predicted from the hydrophobicity plot analysis. These partial peptides may contain either a partial or entire area of one hydrophobic or hydrophilic region.

A partial peptide of the invention can be produced by genetic engineering, known methods of peptide synthesis, or by digesting a protein of the invention with an appropriate peptidase. For peptide synthesis, for example, solid phase synthesis or liquid phase synthesis may be used.

A DNA encoding a protein of the present invention can be used to produce a protein of the present invention in vivo or in vitro as described above. In addition, it may, for example, find application to gene therapy for diseases attributed to genetic abnormality in a gene encoding a protein of the present invention and diseases treatable with a protein of the present invention. Any form of the DNA of the present invention can be used, so long as it encodes a protein of the present invention. Specifically, cDNA synthesized from the mRNA, genomic DNA, or chemically synthesized DNA can be used. The present invention includes a DNA comprising a given nucleotide sequence based on degeneracy of genetic codons, so long as it encodes a protein of the present invention.

The DNA of the present invention can be prepared by methods known to those skilled in the art. For example, a DNA of the present invention can be prepared by preparing a cDNA library from cells which express the protein of the present invention, and conducting hybridization using a partial sequence of a DNA of the invention (e.g. SEQ ID NOs: 1, 3, 5, or 7) as a probe. A cDNA library can be prepared, for example, by the method described in Sambrook, J. et al., Molecular Cloning, Cold Spring Harbor Laboratory Press (1989), or by using commercially available cDNA libraries. A cDNA library can be also prepared by preparing RNA from cells expressing a protein of the present invention, synthesizing cDNA based on the RNA using reverse transcriptase, synthesizing an oligo DNA based on the sequence of the DNA of the present invention (for example, SEQ ID NOs: 1, 3, 5, or 7), conducting PCR by using these as primers, and amplifying cDNA encoding the protein of the present invention.

In addition, by sequencing the nucleotides of the obtained cDNA, a translation region encoded by it can be determined, and an amino acid sequence of a protein of the present invention can be obtained. Moreover, by screening the genomic DNA library using the obtained cDNA as a probe, genomic DNA can be isolated.

More specifically, mRNAs may first be isolated from a cell, tissue, or organ in which a protein of the invention is expressed. Known methods can be used to isolate mRNAs: for instance, total RNA may be prepared by guanidine ultracentrifugation (Chirgwin, J. M. et al., Biochemistry 18:5294-5299 (1979)) or by the AGPC method (Chomczynski, P. and Sacchi, N., Anal. Biochem. 162:156-159 (1987)), and mRNA may then be purified from total RNA using an mRNA Purification Kit (Pharmacia) and such. Alternatively, mRNA may be directly purified by QuickPrep mRNA Purification Kit (Pharmacia).

The obtained mRNA is used to synthesize cDNA using reverse transcriptase. cDNA may be synthesized using a kit such as the AMV Reverse Transcriptase First-strand cDNA Synthesis Kit (Seikagaku Kogyo). Alternatively, cDNA may be synthesized and amplified following the 5'-RACE method (Frohman, M. A. et al., Proc. Natl. Acad. Sci. U.S.A. 85:8998-9002 (1988); Belyavsky, A. et al., Nucleic Acids Res. 17:2919-2932 (1989)) which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform E. coli and such, and a desired recombinant vector is prepared from a selected colony. The nucleotide sequence of the desired DNA can be verified by conventional methods, such as dideoxynucleotide chain termination.

A DNA of the invention may be designed to have a nucleotide sequence that is expressed more efficiently by taking into account the frequency of codon usage in the host to be used for expression (Grantham, R. et al., Nucleic Acids Res. 9:43-74 (1981)). The DNA of the present invention may be altered by a commercially available kit or a conventional method. For instance, the DNA may be altered by digestion with restriction enzymes, insertion of synthetic oligonucleotides or appropriate DNA fragments, addition of a linker, or insertion of the initiation codon (ATG) and/or a stop codon (TAA, TGA, or TAG).

Specifically, DNAs of this invention include DNAs comprising bases A179 through G2305 of the nucleotide sequence of SEQ ID NO: 1, bases A100 through T2172 of the nucleotide sequence of SEQ ID NO: 3, bases A1 through A2130 of the nucleotide sequence of SEQ ID NO: 5, and bases A92 through C2257 of the nucleotide sequence of SEQ ID NO: 7.

Moreover, DNAs of this invention includes DNAs comprising bases A179 through G2305 of the nucleotide sequence of SEQ ID NO: 1, wherein the C1635 has been substituted with T; bases A100 through T2172 of the nucleotide sequence of SEQ ID NO: 3, wherein the A487 has been substituted with G; bases A100 through T2172 of the nucleotide sequence of SEQ ID NO: 3, wherein the T620 has been substituted with C.

Furthermore, the present invention provides DNAs that are capable of hybridizing with a DNA having a nucleotide sequence of SEQ ID NOs: 1, 3, 5, or 7, and encoding a protein having the transporter activity. Suitable hybridization conditions include the above conditions. The hybridizing DNA is preferably a natural DNA, for example, cDNA or chromosomal DNA.

The present invention also relates to a vector into which a DNA of the present invention is inserted. A vector of the present invention is useful for keeping the DNA of the present invention in a host cell, or to express a protein of the present invention.

When E. coli is the host cell and the vector is amplified and produced in large amounts in E. coli (e.g., JM109, DH5α, HB101, or XL1Blue) and such, the vector should have "ori" to be amplified in E. coli and a marker gene for selecting transformed E. coli (for example, a drug-resistance gene selected by a drug (e.g., ampicillin, tetracycline, kanamycin, or chloramphenicol)). For example, M13-series vectors, pUC-series vectors, pBR322, pBluescript, pCR-Script, and so on can be used. Additionally, pGEM-T, pDIRECT, and pT7 can also be used for subcloning and extracting cDNA as well as the vectors described above. When a vector is used to produce a protein of the present invention, an expression vector is especially useful. For example, an expression vector to be expressed in E. coli should have the above characteristics so as to be amplified in E. coli. When E. coli, such as JM109, DH5α, HB101, or XL1 Blue, are used as the host cell, the vector should have a promoter as well as the above characters such as the vector is copied in the host; for example, the lacZ promoter (Ward et al., Nature (1989) 341, 544-546; FASEB J. (1992) 6, 2422-2427), the araB promoter (Better et al., Science (1988) 240, 1041-1043), and the T7 promoter and such can efficiently express the desired gene in E. coli. As such a vector, in addition to the above vectors, pGFX-5X-1 (Pharmacia), "QIAEXPRESS® system" (Qiagen), pEGFP, and pET (in this case, the host is preferably BL21 which expresses T7 RNA polymerase) can be used.

A vector also may contain a signal sequence for polypeptide secretion. As a signal sequence for protein secretion, pelB signal sequence (Lei, S. P. et al., J. Bacteriol. (1987) 169, 4379) can be used in the case of producing protein into the periplasm of E. coli. For introducing a vector into host cells, for example, the calcium chloride method, and the electroporation method can be used.

In addition to E. coli, for example, expression vectors derived from mammals (for example, pcDNA3 (Invitrogen), pEGF-BOS (Nucleic Acids. Res. 1990, 18 (17), p5322), pEF, and pCDM8); expression vectors derived from insect cells (for example, "BAC-TO-BAC® baculovirus expression system" (GIBCO BRL), pBacPAK8); expression vectors derived from plants (for example, pMH1, pMH2), expression vectors derived from animal viruses (for example, pHSV, pMV, pAdexLcw); expression vectors derived from retroviruses (for example, pZIpneo); expression vector derived from yeast (for example, "Pichia Expression Kit" (Invitrogen), pNV11, SP-Q01); and expression vectors derived from Bacillus subtilis (for example, pPL608, pKTH50) can be used to produce a protein of the present invention.

In order to express the vector in animal cells, such as CHO, COS, or NIH3T3 cells, the vector should have a promoter necessary for expression in such cells, for example, the SV40 promoter (Mulligan et al., Nature (1979) 277, 108), the MMLV-LTR promoter, the EF1α promoter (Mizushima et al., Nucleic Acids Res. (1990) 18, 5322), or the CMV promoter, and such, and preferably should also include a marker gene for selecting transformants (for example, a drug resistance gene selected by a drug (e.g., neomycin, G418)). Examples of the vectors with these characteristics include pMAM, pDR2, pBK-RSV, pBK-CMV, pOPRSV, pOp13, and so on.

In addition, in order to stably express a gene and amplify the copy number of the gene in cells, an exemplary method can use the following steps: introducing a vector comprising the complementary DHFR gene (for example pCHO I) into CHO cells in which the nucleic acid synthesizing pathway is deleted, and amplifying by methotrexate (MTX); in the case of transient expression of a gene, an exemplary method can use the steps of transforming with a vector (e.g. pcD) comprising replication origin of SV40 using COS cells comprising the gene expressing SV40 T antigen on chromosomes. The origin used for replication may also be those of polyomavirus, adenovirus, bovine papilloma virus (BPV), and the like. In addition, the expression vector may include a selection marker gene for amplification of the gene copies in host cells. Examples of such markers include, but are not limited to, the aminoglycoside transferase (APH) gene, the thymidine kinase (TK) gene, the E. coli xanthine-guanine phosphoribosyl transferase (Ecogpt) gene, and the dihydrofolate reductase (dhfr) gene.

On the other hand, a DNA of the present invention can be expressed in vivo in animals, for example, by inserting a DNA of the present invention into an appropriate vector and introducing it into the living body by a method such as the retrovirus method, the liposome method, the cationic liposome method, or the adenovirus method. By using these, gene therapy against diseases attributed to the mutation of a transporter gene of the present invention can be effected. As a vector to be used, for example, adenovirus vector (for example pAdexlcw), and retrovirus vector (for example, pZIPneo) can be used; however, the present invention is not restricted thereto. Common gene manipulation, for example, insertion of the DNA of the present invention to a vector, can be performed according to conventional methods (Molecular Cloning, 5. 61-5. 63). Administration into a living body can be either an ex vivo method, or in vivo method.

The present invention also relates to a transformed cell into which a DNA or a vector of the present invention has been introduced. The host cell into which the vector of the invention is introduced is not particularly limited. For example, E. coli or various animal cells can be used. The transformed cells of the present invention can be used as, for example, a production system for producing or expressing a protein of the present invention. The present invention provides methods of producing a protein of the invention both in vitro or in vivo. For in vitro production, eukaryotic cells or prokaryotic cells can be used as host cells.

Eukaryotic cells useful as host cells may be animal, plant, or fungi cells. As animal cells, mammalian cells, such as CHO (J. Exp. Med. 108:945 (1995)), COS, 3T3, myeloma, baby hamster kidney (BHK), HeLa, and Vero cells; or amphibian cells, such as Xenopus oocytes (Valle, et al., Nature 291:340-358 (1981)); or insect cells, such as Sf9, Sf21, or Tn5 cells, can be used. CHO cells lacking the DHFR gene (dhfr-CHO) (Proc. Natl. Acad. Sci. U.S.A. 77:4216-4220 (1980)) or CHO K-1 (Proc. Natl. Acad. Sci. U.S.A. 60:1275 (1968)) may also be used. In animal cells, CHO cells are particularly preferable for mass expression. A vector can be introduced into host cells by, for example, the calcium phosphate method, the DEAF dextran method, the cationic liposome DOTAP (Boehringer Mannheim), the electroporation method, the lipofection method, and such. A recombinant protein derived from the obtained transformants can be purified by standard methods, for example, the method described in "The Qiaexpressionist handbook, Qiagen, Hilden, Germany".

As plant cells, plant cells originating from *Nicotiana tabacum* are known as protein-production system, and may be used as callus cultures. As fungi cells, yeast cells, such as *Saccharomyces*, including *Saccharomyces cerevisiae*, or filamentous fungi, such as *Aspergillus*, including *Aspergillus niger*, are known and may be used herein.

Prokaryotic cells suitable for use in the production system of the present invention include, but are not limited to, bacterial cells. A known example of these bacterial cells is *E. coli*, such as JM109, DH5α, HB101. Regarding others, *Bacillus subtilis* is known in the art.

These cells are transformed by a desired DNA, and the resulting transformants are cultured in vitro to obtain the protein. Transformants can be cultured using known methods. Culture medium for animal cells, for example, DMEM, MEM, RPMI1640, or IMDM, may be used with or without serum supplement, such as fetal calf serum (FCS). The pH of the culture medium is preferably between about pH 6 to 8. Such cells are typically cultured at about 30 to 40° C. for about 15 to 200 hr, and the culture medium may be replaced, aerated, and/or stirred if necessary.

On the other hand, animal and plant hosts may be used for in vivo production. For example, a desired DNA can be introduced into an animal or plant host. Encoded proteins are produced in vivo, and then recovered. These animal and plant hosts are included in the host cells of the present invention.

Animals to be used for the production system described above include, but are not limited to, mammals and insects. Mammals such as goat, porcine, sheep, mouse, and bovine may be used (Vicki Glaser, SPECTRUM Biotechnology Applications (1993)). Alternatively, the mammals may be transgenic animals.

For instance, a desired DNA may be prepared as a fusion gene with a gene encoding a protein specifically produced into milk, such as goat β casein. DNA fragments, comprising the fusion gene having the desired DNA, are injected into goat embryos, which are then introduced back to female goats. Proteins are recovered from milk produced by the transgenic goats (i.e., those born from the goats that had received the modified embryos) or from their offspring. To increase the amount of milk containing the proteins produced by transgenic goats, appropriate hormones may be administered to them (Ebert, K. M. et al., Bio/Technology 12:699-702 (1994)).

Alternatively, insects, such as the silkworm, may be used. Baculovirus inserted a DNA encoding a desired protein can be used to infect silkworms, and the desired protein is recovered from their body fluid (Susumu, M. et al., Nature 315: 592-594 (1985)).

As plants, for example, tobacco can be used. In use of tobacco, a DNA encoding a desired protein may be inserted into a plant expression vector, such as pMON530, which is then introduced into bacteria, such as *Agrobacterium tumefaciens*. Then, the bacteria is used to infect a tobacco plant, such as *Nicotiana tabacum*, and a desired polypeptide is recovered from the plant's leaves (Julian K.-C. Ma et al., Eur. J. Immunol. 24:131-138 (1994)).

A protein of the present invention obtained as above may be isolated from the interior or the exterior (e.g., the culture medium) of transformed cells, and purified as a substantially pure homogeneous protein. The method for protein isolation and purification is not limited to any specific method; in fact, any standard method may be used. For instance, column chromatography, filter, ultrafiltration, salting-out, solvent precipitation, solvent extraction, distillation, immunoprecipitation, SDS-polyacrylamide gel electrophoresis, isoelectric point electrophoresis, dialysis, recrystallization, and such may be appropriately selected and combined to isolate and purify the protein.

For chromatography, for example, affinity chromatography, ion-exchange chromatography, hydrophobic chromatography, gel filtration, reverse-phase chromatography, adsorption chromatography, and such may be used (Strategies for Protein Purification and Characterization: A Laboratory Course Manual. Ed. Daniel R. Marshak et al., Cold Spring Harbor Laboratory Press (1996)). These chromatographies may be performed by liquid-phase chromatography, such as HPLC and FPLC. Thus, the present invention provides for highly purified proteins produced by the above methods.

A protein of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, and glucosidase.

The present invention also provides antibodies that bind to the proteins of the invention. An antibody of the invention can be used in any form, such as monoclonal or polyclonal antibodies, and includes antiserum obtained by immunizing a rabbit with a protein of the invention, all classes of polyclonal and monoclonal antibodies, human antibodies, and humanized antibodies produced by genetic recombination.

A protein of the invention used as an antigen to obtain an antibody may be derived from any animal species, but preferably from a mammal such as a human, mouse, or rat, or more preferably from a human. A human-derived protein may be obtained from the nucleotide or amino acid sequences disclosed herein.

In the present invention, a protein to be used as an immunization antigen may be a complete protein or a partial peptide of the protein. A partial peptide may be, for example, an amino (N)-terminal or carboxy (C)-terminal fragment of the protein. Herein, "an antibody" is defined as a molecule that specifically reacts with either the full-length protein or a fragment of the protein.

A gene encoding a protein of the invention or its fragment may be inserted into a known expression vector, which may then be used to transform a host cell as described herein. The desired protein or its fragment may be recovered from the exterior or the interior of the transformed host cells, by any standard method, and may be used as an antigen. Alternatively, cells expressing the protein or their lysates, or a chemically synthesized protein of the present invention may be used as an antigen.

Any mammalian animal may be immunized with the antigen, but preferably the compatibility with parental cells used for cell fusion is taken into account. In general, animals of the Rodentia order, Lagomorphs, or Primates may be used.

Animals of the order Rodentia include, for example, mouse, rat, and hamster. Lagomorphs include, for example, rabbit. Primates include, for example, a monkey of catarrhine (old world monkey) such as *Macaca fascicularis*, rhesus monkey, sacred baboon, or chimpanzee.

Methods for immunizing animals against antigens are known in the art. Intraperitoneal injection or subcutaneous injection of antigens is used as a standard method for immunization of mammals. More specifically, antigens may be diluted and suspended in an appropriate amount with phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined for increase of the amount of desired antibodies by a standard method.

Polyclonal antibodies against the proteins of the present invention may be prepared by collecting blood from the immunized mammal examined for the increase of desired antibodies in the serum, and by separating serum from the blood by any conventional method. Polyclonal antibodies may be used as serum containing the polyclonal antibodies, or if necessary, a fraction containing the polyclonal antibodies may be isolated from the serum. Immunoglobulin G or M can be prepared by obtaining a fraction which recognizes only the protein of the present invention using an affinity column coupled with the protein of the present invention and further purifying this fraction by using protein A or protein G column.

To prepare monoclonal antibodies, immune cells are collected from the mammal immunized against the antigen and checked for increased level of desired antibodies in the serum as described above, and are subjected to cell fusion. The immune cells used for cell fusion are preferably obtained from spleen. As the other parental cells to be fused with the above immunocyte, for example, preferably myeloma cells of mammalians, more preferably myeloma cells which acquired the property for selecting fused cells by drugs, can be used.

The above immunocyte and myeloma cells can be fused by known methods, for example, the method by Milstein et al. (Galfre, G. and Milstein, C., Methods Enzymol. (1981) 73, 3-46).

Resulting hybridomas obtained from cell fusion may be selected by cultivating them in a standard selection medium, such as HAT medium (culture medium containing hypoxanthine, aminopterin, and thymidine). The cell culture is typically continued in the HAT medium for several days to several weeks, the sufficient time to allow all the other cells, except desired hybridoma (non-fused cells), to die. Then, by the standard limiting dilution method, a hybridoma cell producing the desired antibody is screened and cloned.

In addition to the above method, in which a non human animal is immunized against an antigen for preparing hybridoma, human lymphocytes, such as that infected by EB virus, may be immunized with a protein, protein-expressing cells, or their lysates in vitro. Then, the immunized lymphocytes are fused with human-derived myeloma cells capable of indefinitely dividing, such as U266, to yield a hybridoma producing a desired human antibody having binding activity to the protein (Unexamined Published Japanese Patent Application (JP-A) No. Sho 63-17688).

Next, the monoclonal antibody obtained by transplanting the obtained hybridomas into the abdominal cavity of a mouse and by extracting ascites can be purified by, for example, ammonium sulfate precipitation, protein A or protein G column, DEAF ion exchange chromatography, or an affinity column to which the protein of the present invention is coupled. An antibody of the present invention can be used not only for purification and detection of the protein of the present invention, but also as a candidate agonist or antagonist of a protein of the present invention. In addition, the antibody can be utilized in antibody treatment for diseases associated with a protein of the present invention. When the obtained antibody is used for the administration to the human body (antibody treatment), a human antibody or a humanized antibody is preferable for reducing immunogenicity.

For example, transgenic animals having a repertory of human antibody genes may be immunized against a protein, protein-expressing cells, or their lysates as an antigen. Antibody-producing cells are collected from the animals, and fused with myeloma cells to obtain hybridoma, from which human antibodies against the protein can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck, C. A. K. and Larrick, J. W., THERAPEUTIC MONOCLONAL ANTIBODIES, published in the United Kingdom by MACMILLAN PUBLISHERS LTD (1990)). A DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the proteins of the invention. For instance, the antibody fragment may be Fab, $F(ab')_2$, Fv, or single chain Fv (scFv), in which Fv fragments from H and L chains are ligated by an appropriate linker (Huston, J. S. et al., Proc. Natl. Acad. Sci. U.S.A. 85:5879-5883 (1988)). More specifically, an antibody fragment may be generated by treating an antibody with an enzyme such as papain or pepsin. Alternatively, a gene encoding the antibody fragment may be constructed, inserted into an expression vector, and expressed in an appropriate host cell (see, for example, Co, M. S. et al., J. Immunol. 152:2968-2976 (1994); Better, M. and Horwitz A. H., Methods Enzymol. 178:476-496 (1989); Pluckthun, A. and Skerra, A., Methods Enzymol. 178:497-515 (1989); Lamoyi, E., Methods Enzymol. 121:652-663 (1986); Rousseaux, J. et al., Methods Enzymol. 121:663-669 (1986); Bird, R. E. and Walker, B. W., Trends Biotechnol. 9:132-137 (1991)).

An antibody may be modified by conjugation with a variety of molecules, such as polyethylene glycol (PEG). The term "an antibody" as used herein includes such modified antibodies. The modified antibody can be obtained by chemically modifying an antibody. These modification methods are conventional in this field.

Alternatively, an antibody of the present invention may be obtained as a chimeric antibody by using known technique, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region.

Obtained antibodies may be purified into homogeneity. An antibody used in the present invention can be separated and purified by the method used for separating and purifying usual proteins. For example, the separation and purification of the protein can be performed by the appropriately selected and combined use of column chromatography such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but the methods are not limited thereto. The level of the obtained antibody can be determined by measurement of absorbance, enzyme-linked immunosorbent assay (ELISA), and such.

Examples of columns used for affinity chromatography include protein A column and protein G column. Examples of columns using protein A column include HYPERD®, POROS®, SEPHAROSE® Fast Flow (F. F.) (Pharmacia), etc.

In addition to affinity chromatography, chromatography includes, for example, ion-exchange chromatography, hydrophobic chromatography, gel filtration, reverse-phase chromatography, adsorption chromatography, and such (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography such as HPLC, FPLC, and so on.

For example, measurement of absorbance, enzyme-linked immunosorbent assay (ELISA), enzyme immunoassay (EIA), radioimmunoassay (RIA), and/or immunofluorescence may be used to measure the antigen binding activity of the antibody of the invention. In ELISA, an antibody of the present invention is immobilized on a plate, protein of the invention is applied to the plate, and then a sample containing a desired antibody, such as culture supernatant of antibody-producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment, may be used as a protein. BIAcore (Pharmacia) may be used to evaluate the activity of the antibody according to the present invention.

The above methods allow for the detection or measurement of a protein of the invention, by exposing an antibody of the invention to a sample assumed to contain a protein of the invention, and detecting or measuring the immune complex formed by the antibody and the protein. Because the method of detection or measurement of proteins according to the invention can specifically detect or measure proteins, the method may be useful in a variety of experiments in which the protein is used.

The present invention also provides a polynucleotide comprising at least 15 nucleotides which is complementary to a DNA encoding a human "OATP-B", "OATP-C", "OATP-D", or "OATP-E" protein (SEQ ID NOs: 1, 3, 5, or 7), or complementary strand thereof.

Herein, the term "complementary strand" is defined as one strand of a double strand DNA composed of A:T and G:C base pair to the other strand. Also, "complementary" is defined as not only those completely matching within a continuous region of at least 15 nucleotides, but also those having a homology of at least 70%, preferably at least 80%, more preferably 90%, and still more preferably 95% or more within that region. The homology may be determined using the algorithm described herein.

Such nucleotide includes, probes, primers, nucleotides and nucleotide derivatives (for example, antisense oligonucleotides, ribozymes, and so on) for inhibiting the expression of a protein of the present invention, which are used to detect or amplify DNA encoding a protein of the invention. Moreover, such DNA can be utilized in preparation of DNA chip.

When used as primers, such nucleic acids are complementary at the 3'-end, and restriction enzyme recognition sequences or tags can be added to the 5'-end.

The antisense oligonucleotides of the present invention include nucleotides that hybridize with any site within the nucleotide sequence any one of SEQ ID NOs: 1, 3, 5, and 7. An antisense oligonucleotide is preferably against at least 15 continuous nucleotides in the nucleotide sequence any one of SEQ ID NO: 1, 3, 5, or 7. The above-mentioned antisense oligonucleotide, which contains an initiation codon in the above-mentioned at least 15 continuous nucleotides, is even more preferred.

Derivatives or modified products of antisense oligonucleotides can be used as antisense oligonucleotides. Examples of such modified products are lower alkyl phosphonate modifications, such as methyl-phosphonate-type or ethyl-phosphonate-type; phosphothioate modifications; and phosphoamidate modifications.

The term "antisense oligonucleotides" as used herein means, not only those in which the entire nucleotides corresponding to those constituting a specified region of a DNA or mRNA are complementary, but also those having a mismatch of one or more nucleotides, so long as DNA or mRNA and an oligonucleotide can specifically hybridize with the nucleotide sequence of SEQ ID NO: 1, 3, 5, or 7.

An antisense oligonucleotide derivative of the present invention has inhibitory effect on the function of a protein of the present invention wherein the derivative inhibits the expression of the protein of the invention by acting upon cells producing the protein of the invention and by binding to the DNA or mRNA encoding the protein to inhibit its transcription or translation or to promote the degradation of the mRNA.

An antisense oligonucleotide derivative of the present invention can be made into an external preparation, such as a liniment or a poultice, by mixing with a suitable base material which is inactive against the derivatives.

Also, as necessary, the derivatives can be formulated into tablets, powders, granules, capsules, liposome capsules, injections, solutions, nose-drops, and freeze-drying agents, and such by adding excipients, isotonic agents, solubilizing agents, stabilizers, preservative substance, pain-killers, and such. These can be prepared by following usual methods.

An antisense oligonucleotide derivative of the present invention is given to the patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin, or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

An antisense oligonucleotide of the invention inhibits the expression of a protein of the invention and is thereby useful for suppressing the biological activity of the protein. Also, expression-inhibitors comprising the antisense oligonucleotide of the invention are useful in that they can inhibit the biological activity of a protein of the invention.

The transporter proteins of this invention can be used to control internal absorption and dynamics of drugs. Based on the results of detailed analysis of the substrate specificity of transporter proteins of this invention, drugs can be designed so as to be transported by these transporters and internal absorbability of the drugs mediated by these transporter proteins can be improved. Conventional modifications to enhance fat-solubility are no longer necessary for drugs so designed, which enables the speedy and efficient development of water-soluble drugs that are easy to handle. The drugs thus developed are thought to be absorbed principally depending on the internal distribution pattern of transporter proteins of this invention, and an organ-specific delivery of the drugs thus becomes possible. In particular, if the transporter proteins of this invention are distributed in the target organ of the drug, an ideal drug delivery system (DDS) can be developed. If a drug is to be absorbed mediated by not the transporter proteins of this invention but other transporters, the drug can be designed so as to be specific to other transporter proteins by designing it considering the substrate specificity of the transporter proteins of this invention. For example, it has been revealed that the OATP-E gene is expressed in high frequency in a variety of solid cancer cells but seldom in hemocytes. Therefore, anticancer agents can be obtained by constructing a screening system using the OATP-E gene to screen compounds which are specifically transported into cells mediated by the OATP-E protein; these agents are expected to be anticancer agents with reduced cytotoxicity to hemocytes.

Screening of compounds which are transported into cells from the outside of the cells mediated by a protein of the present invention can be carried out, for example, as follows. First, cells are provided which express a protein of this invention on their cell membranes. More specifically, for example, a vector to express a protein of this invention may be constructed and transferred into appropriate cells. Then, a labeled compound to be tested is brought into contact with said cells. For example, low molecular weight compounds can be used as compounds to be tested. There is no particular limitation on the label used for labeling the compounds to be tested, so long as it can be readily detected; for example, radiolabels, fluorescence labels, and such can be used. Then, labeled test compounds which are taken up into said cells are detected. The detection can be performed by measuring radioactivity using a liquid scintillation counter, and such in case of radiolabeled compounds, and fluorescence using a fluorometer, etc. in case of fluorescence labeled compounds. In addition, even when using non-labeled compounds, the amount of the compounds which has been transported into the cell mediated by a protein of the present invention can be measured by the bioassay relied biological activities (e.g. cytotoxicity, cell proliferation stimulating activity), and such of said compounds as the indicator. Then, based on the results of the above-described detection, the compound taken up into cells is selected. Specifically, in this screening, the detection system for the transport activity as described in Example 3 can be used. Compounds thus isolated can be used to create the above-described drugs.

Another possible application of this invention is to develop a drug that targets the transporter proteins of this invention. The transporters play important roles in the absorption mechanism of nutrients and drugs, or the excretion mechanism of drugs and internal metabolites. Thus, damage or abnormal elevation of the transporter's functions may cause some disorders. It is considered to be efficacious against such disorders to administer a drug containing a compound that inhibits or enhances functions of the transporter proteins of this invention, or regulates the expression level of the transporter gene of this invention and the amount of the transporter proteins.

Screening of compounds which promote or inhibit the transporter activity of the proteins of this invention can be carried out, for example, as follows. First, cells are provided which express one or more of the proteins of this invention on their cell membranes. Then, a test compound and a labeled organic compound which is transported through the intermediary of the proteins of this invention are brought into contact with said cells. Examples of organic compounds to be used include estradiol-17β-glucuronide, estron-3-sulfate, benzyl penicillin, prostaglandin E2, and such, but the present invention is not limited to them. Then, the amount of labeled organic compound which has been taken up into said cells is measured. Then, a compound is selected which increases or decreases the amount of the labeled organic compound taken up into said cell compared with that in case of a similar measurement conducted in the absence of a test compound (control). Specifically, in this screening, the detection system for the transport activity as described in Example 3 can be used. As a result, when the amount of labeled organic compound to be taken up into said cells is increased by the contact with a test compound, said compound is judged to promote the activity of a protein of this invention to transport the organic compound. On the other hand, when the amount of labeled organic compound to be taken up into said cells is decreased by the contact with a compound to be tested, said compound is judged to inhibit the activity of a protein of this invention to transport the organic compound.

Compounds thus obtained by the screening method of this invention may be applied to drug therapy using a protein of this invention and treatment mediated by the control of substance transport by the protein. The structure of compounds obtained by the screening method of this invention may be partially modified by addition, deletion and/or substitution.

When a compound binding to a protein of the invention, a protein of the invention, and a partial peptide thereof are used as a pharmaceutical for humans and other mammals, such as mice, rats, guinea pigs, rabbits, chicken, cats, dogs, sheep, pigs, bovines, monkeys, baboons, chimpanzees, the protein or the isolated compound can be administered not only directly, but also in a dosage form using known pharmaceutical preparation methods. For example, according to needs, the drugs can be taken orally, as sugarcoated tablets, capsules, elixirs, and microcapsules, or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agent, surface-active agent, stabilizers, flavoring agents, excipients, vehicles, preservatives, binders, and such into a unit dose form required for generally accepted drug implementation. The amount of active ingredient in these preparations makes a suitable dosage within the indicated range acquirable.

Examples of additives which can be mixed to tablets and capsules include: binders, such as gelatin, corn starch, tragacanth gum, and gum acacia; excipients, such as crystalline cellulose; swelling agents, such as corn starch, gelatin, and alginic acid; lubricants, such as magnesium stearate; sweeteners, such as sucrose, lactose, or saccharin; and flavoring agents, such as peppermint, *Gaultheria adenothrix* oil, and cherry. When the unit dosage form is a capsule, a liquid carrier, such as oil, can also be included in the above ingredients. Sterile composites for injections can be formulated following normal drug implementations using vehicles such as distilled water used for injections.

Physiological saline, glucose, and other isotonic liquids, including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, and non-ionic surfactants, such as Polysorbate 80™ and HCO-50.

Sesame oil or soy-bean oil can be used as an oleaginous liquid and may be used in conjunction with benzyl benzoate or benzyl alcohol as solubilizers; alternatively, they may be formulated with a buffer such as phosphate buffer and sodium acetate buffer, a pain-killer such as procaine hydrochloride, a stabilizer such as benzyl alcohol and phenol, and an antioxidant. The prepared injection may then be filled into a suitable ampule.

Methods well known to those skilled in the art may be used to administer the pharmaceutical compounds of the present invention to patients. Examples of suitable administration methods include intraarterial, intravenous, subcutaneous injections and also as intranasal, transbronchial, intramuscular, percutaneous, or oral administrations. The dosage varies according to the body-weight and age of a patient and the administration method, but one skilled in the art can suitably select them. If the compound can be encoded by a DNA, the DNA can be inserted into a vector for gene therapy and perform the therapy. The dosage and method of administration vary according to the body-weight, age, and symptoms of a patient, but one skilled in the art can select them suitably.

The DNAs of this invention can be applied to gene therapy for disorders caused by aberrations in the activity and expression level of the proteins of this invention. In the case of using DNA in gene therapy, a DNA of this invention is inserted to an adenovirus vector (e.g. pAdexLcw), a retrovirus vector (e.g. pZIPneo), and such for administration into the living body. The transformed vector may be administered into the living body by the ex vivo method or in vivo method. Gene therapy can also be performed by administering a synthetic antisense DNA to the living body either directly or after being inserted into above-described vectors. The DNAs of this invention can be applied also to the diagnosis for disorders caused by aberrant activities and expression levels of the proteins of this invention.

BEST MODE FOR CARRYING OUT THE INVENTION

Figure 1:
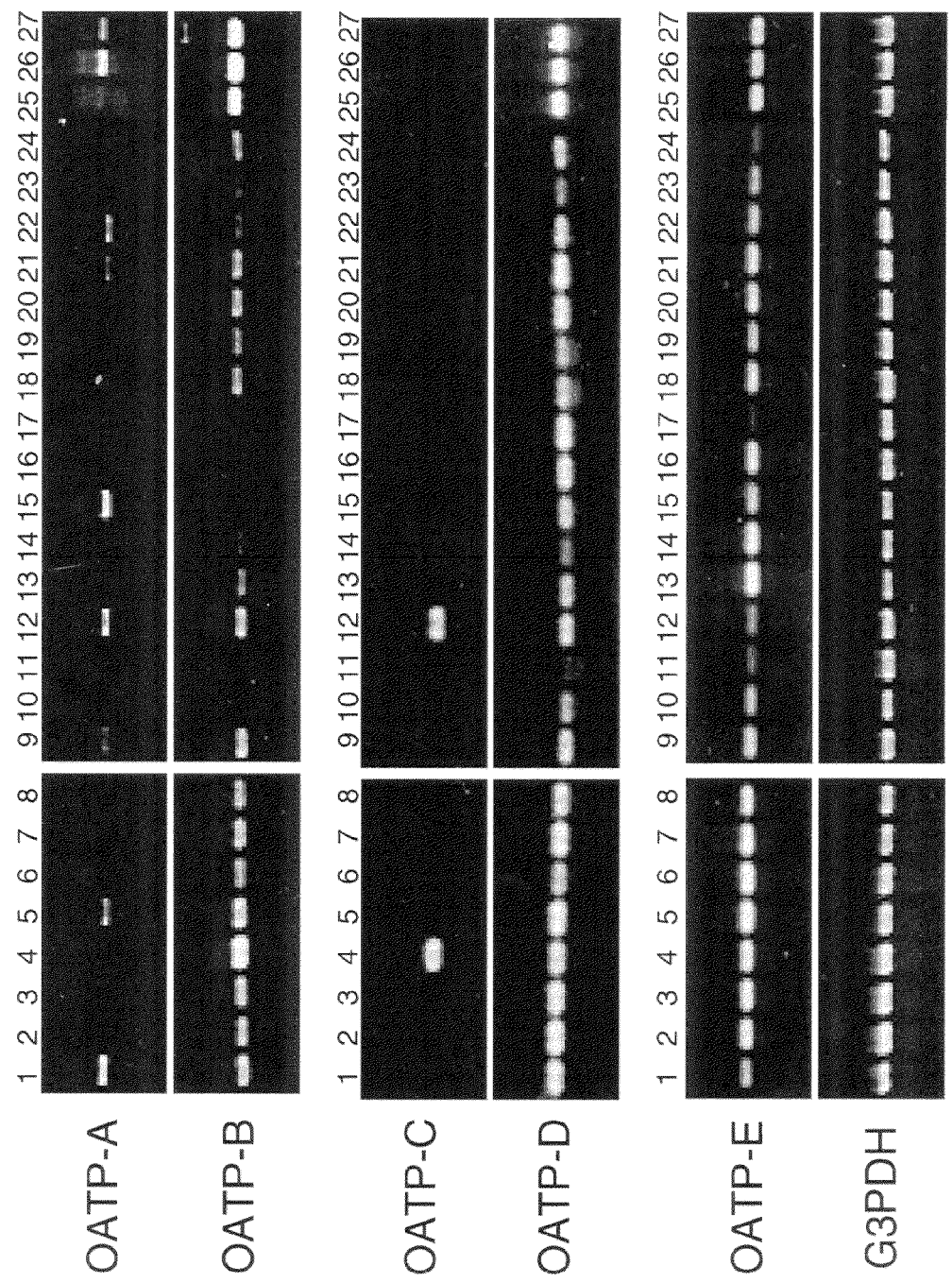
FIG. 1 is a photograph showing the results of examination by the RT-PCR method for the expression level of respective OATP family genes in human fetal and adult tissues: 1. fetal brain, 2. fetal heart, 3. fetal kidney, 4. fetal liver, 5. fetal lung, 6. fetal skeletal muscle, 7. fetal spleen, 8. fetal thymus, 9. adult pancreas, 10. adult kidney, 11. adult skeletal muscle, 12. adult liver, 13. adult lung, 14. adult placenta, 15. adult brain, 16. adult heart, 17. adult peripheral blood leukocytes, 18. adult large intestine, 19. adult small intestine, 20. adult ovary, 21. adult testis, 22. adult prostate, 23. adult thymus, 24. adult spleen, 25. adult bone marrow, 26. adult lymph node, and 27. adult tonsil.

The present invention is described below in more detail with reference to examples, but is not construed as being limited thereto. Molecular biological experimental techniques in general have been performed principally according to methods described in usual experimental textbooks, such as "Sambrook, J., Fritsch, E. F., Maniatis, T., Molecular Cloning, Cold Spring Harbor Lab. press (1989)".

Example 1

Cloning of cDNAs Comprising the Entire Open Reading Frame (ORF) of OATP-B, C, D, or E Gene

OATP-B

The OABE-1 primer (5' gat aag ctt ctg tgt ggc cca aga aga act gac 3'/SEQ ID NO: 9) and OABE-6 primer (5' gat aag ctt tac tgc tgt ggc tgc tac tct tgg 3'/SEQ ID NO: 10) were prepared based on the nucleotide sequences of W19504 and AI052501, ESTs possibly encoding the amino acid sequence having significant homology with the human OATP-A protein. Using these primers, PCR was performed against human adult brain polyA+ RNA-derived cDNA as a template to amplify the OATP-B cDNA comprising the entire ORF. The OATP-B cDNA thus amplified by PCR was cleaved at the Hind III site added to the primer, and incorporated into the Hind III site of the pcDNA3 vector (Invitrogen), an expression vector for mammalian cells. By sequencing a plurality of clones, a clone (pcDNA3/OATP-B) with no PCR error was selected to be used in expression experiments.

OATP-C

Respective primers were prepared from the nucleotide sequences of the following ESTs possibly encoding amino acid sequences having a significant homology with the human OATP-A:

```
EST H62893:
2893-4 primer
(5' aag ctt ccg tca ata aaa cca aca 3'/
SEQ ID NO: 11),
and 28931 primer
(5' ctt ctc ttg ttg gtt tta ttg acg 3'/
SEQ ID NO: 12);
```

```
EST R29414;
94142 primer
(5' tgt aag tta ttc cat tgt ttc cac 3'/
SEQ ID NO: 13);
and EST T73863;
38631 primer
(5' ttg gtg ctt tta ctt atg tct tca 3'/
SEQ ID NO: 14).
```

Using these primers, the human OATP-C divided into three fragments was cloned.

The 5'-end fragments were cloned by the 5' Rapid Amplification cDNA Ends (RACE) method. More specifically, polymerase chain reaction (PCR) was performed against the human fetal liver-derived MARATHON READY™ cDNA (CLONTECH) as a template using a combination of the AP1 primer, a linker primer attached to the kit, and the 2893-4 primer to amplify the 5'-end fragment of the human OATP-C cDNA of about 400 bp. This cDNA fragment was incorporated into the pT7Blue-T vector (Novagen) by the TA cloning method, and a plurality of subclones thus obtained were sequenced to determine the 5'-end sequence of the human OATP-C cDNA. The 3'-end sequence was similarly cloned by the 3' RACE method. Specifically, PCR was performed with the human fetal liver-derived MARATHON READY™ cDNA (CLONTECH) as a template using a combination of the AP1 primer, a linker primer attached to the kit, and the 3863-1 primer to amplify the 3'-end fragment of the human OATP-C cDNA of about 1.5 kbp. This cDNA fragment was incorporated into the pT7Blue-T vector by the TA cloning method, and a plurality of subclones thus obtained were sequenced to determine the 3'-end sequence of the human OATP-C cDNA. In addition, the intermediate fragment between the 5'-end sequence and the 3'-end sequence was amplified by PCR with cDNA derived from the human adult liver as a template using a combination of the 2893-1 and 9414-2 primers. The fragment of about 1.2 kbp thus obtained was purified by the gel filtration method and directly sequenced to determine the nucleotide sequence. By combining the obtained sequences, the cDNA sequence comprising the entire open reading frame (ORF) of human OATP-C was determined.

The expression plasmid was constructed as follows. The human OATP-C was divided into two fragments, and they were amplified by PCR with the human adult liver-derived cDNA as a template using a combination of the following primers:

```
5'-end
OAHC17 primer
(5' gat ggt acc aaa ctg agc atc aac aac aaa
aac 3'/SEQ ID NO: 15),
and OAHC18 primer
(5' gat ggt acc cat cga gaa tca gta gga gtt
atc 3'/SEQ ID NO: 16).

3'-end
OAHC21 primer
(5' gat ggt acc tac cct ggg atc tct gtt ttc
taa 3'/SEQ ID NO: 17),
and OAH022 primer
(5' gat ggt acc gtt tgg aaa cac aga agc aga
agt 3'/SEQ ID NO: 18).
```

These fragments were subcloned into the pT7Blue-T vector, respectively, to select clones with no PCR error. After both clones were linked at the Bgl II sites existing in the overlapping regions, the product was cleaved at the Kpn I sites existing at both ends, and incorporated into the Kpn I site of the pcDNA3 vector to obtain the expression plasmid, pcDNA3/OATP-C.

OATP-D 0224-3 primer (5' cgc cct cgt ggt ttt tga tgt agc 3'/SEQ ID NO: 19) was prepared from EST AA280224, an EST possibly encoding the amino acid sequence having significant homology with the human OATP-A protein. Furthermore, it was found that a partial sequence of the PAC clone (pDJ430i19) derived from q26.1 region of human chromosome 15 could also encode the amino acid sequence having significant homology with the human OATP-A protein. PAC151-2 primer (5' gcg gtg cct tac tct tct tct ctt 3'/SEQ ID NO: 20) was prepared from this sequence. PCR was performed using these primers on the human adult brain-derived cDNA as a template to amplify a cDNA fragment of about 1.1 kbp. Using this cDNA fragment as a probe, the human adult kidney-derived 5'-STRETCH PLUS cDNA library (CLONTECH) was screened by the plaque hybridization method. PCR was performed with a phage suspension of obtained positive clones as a template using a combination of the above-described primers, or OATP-D gene specific primer prepared from the above-elucidated sequence and GT10 S1 primer (5' ctt ttg agc aag ttc agc ct 3'/SEQ ID NO: 21) or GT10 A1 primer (5' aga ggt ggc tta tga gta ttt ctt 3'/SEQ ID NO: 22) prepared from the sequence of λgt-10 vector, and the fragments thus amplified were directly sequenced to determine the nucleotide sequence. Furthermore, the region covered by the phage clone was extended to determine the entire ORF sequence by the screening using the DNA fragment comprising the newly obtained region as a probe.

OATP-E 7130-1 primer (5' tgt aca agg tgc tgg gcg tcc tct 3'/SEQ ID NO: 23) and 7130-4 primer (5' cga tcg ggt ata aaa cac att cta 3'/SEQ ID NO: 24) were prepared from EST AI347130, an EST potentially encoding the amino acid sequence having significant homology with the human OATP-A protein. PCR was performed using these primers with the human adult lung-derived cDNA as a template to amplify a cDNA fragment of about 400 bp. The human adult kidney-derived 5'-STRETCH PLUS cDNA library (CLONTECH) was screened using this cDNA as a probe by the plaque hybridization method. PCR was performed with a phage suspension of obtained positive clones as a template using a combination of the above-described primers or the OATP-E gene specific primer prepared from the above-elucidated sequence and the GT10-S1 primer or GT10-A1 primer prepared from the λgt-10 vector sequence, and amplified fragments thus obtained were directly sequenced to determine the nucleotide sequence. Furthermore, the region covered by the phage clone was extended to determine the entire ORF sequence by the screening using the DNA fragment comprising the newly obtained region as a probe.

The expression plasmid was constructed as follows. The human OATP-E was divided into two fragments, 5'-end and 3'-end fragments, which were amplified by PCR using combinations of the following primers. The 5'-end fragment was amplified using human adult lung-derived cDNA as a template, and the 3'-end fragment was amplified using human fetal lung-derived cDNA as a template, respectively.

5'-end:
OAE17 primer
(5' gat aag ctt tgc gtg gct gaa gcc tcg aag tca 3'/SEQ ID NO: 25),
and OAE18 primer
(5' gat gga tcc act ggt gca ttt ccg ccg ctc tca 3'/SEQ ID NO: 26).

3'-end:
OAE21 primer
(5' gat aag ctt tct tca ccg ccg ttc cca tcc ttg 3'/SEQ ID NO: 27),
and OAE22 primer
(5' gat gga tcc act gtt ctg tca tca gga aat gct 3'/SEQ ID NO: 28).

These fragments were subcloned into the Hind III/BamH I site of the pcDNA3 vector, respectively, to select clones with no PCR error. Both clones were linked at the BstP I sites existing in the overlapping regions to obtain the expression plasmid, pcDNA3/OATP-E.

PCR
PCR was fundamentally performed under the following basic conditions with appropriate modifications if necessary.
<Composition of Reaction Solution>
template DNA,
10× EX TAQ™ buffer (TaKaRa) 5 µl,
2.5 mM dNTPs (TaKaRa) 4 µl,
EX TAQ™(TaKaRa) 0.5 µl,
TAQSTART™ Antibody (CLONTECH) 0.5 µl,
sense primer 10 to 20 pmol, and
antisense primer 10 to 20 pmol
/total volume 504
<Reaction Conditions>
PCR in General:
94° C., 2 min→(94° C., 30 s→55 to 62° C., 30 s→72° C., 2 to 3 min)×25 to 40 cycles→72° C., 10 min.
RACE Method:
94° C., 2 min→(94° C., 30 s→68° C., 4 min)×5 cycles→(94° C., 30 s→62° C., 30 s→72° C., 2 min)×30 cycles→72° C., 10 min.

Synthesis of cDNA cDNAs used as templates for PCR were prepared using the SUPERSCRIPT® II RNase H⁻ reverse transcriptase (GIBCO BRL) according to the usual method recommended by the supplier. Specifically, 10 µg of the total RNA or 2 µg of poly A⁺ RNA and about 1 µg of the oligo dT primer (GIBCO BRL) or about 0.5 µg of the random hexamer primer (GIBCO BRL) were mixed, heated at 70° C. for 10 min, and then cooled on ice. The first strand buffer (GIBCO BRL), dithiothreitol (DDT), (final concentration of 10 mM), dNTPs (final concentration of 0.5 mM; GIBCO BRL), and 400 to 800 U of SUPERSCRIPT® II RNase H⁻ reverse transcriptase were added to this mixture, and the resulting mixture was warmed at 42° C. for 1 h to synthesize cDNA. The mixture was then heated at 70° C. for 15 min, and a portion thereof was used as the template.

Hybridization

DNA fragments amplified by PCR, or purified from gels after agarose electrophoresis, and such were labeled with [α-$^{32}$P]dCTP using the READY TO GO™ DNA labeling beads (Pharmacia) by the random primer method to be used as the primer. The hybridization was performed using the EXPRESSHYB™ Hybridization Solution (CLONTECH) by heating at 68° C. for 2 h or more according to the method recommended by the supplier. After the hybridization, the filter was washed twice in a solution of 2×SSC and 0.1% SDS solution at room temperature for 20 min, and then, twice in a solution of 0.1×SSC and 0.1% SDS at 50° C. for 20 min.

Example 2

Analysis by RT-PCR Method

Using the following primers specific for respective genes, the tissue distribution of the expression of each gene was analyzed by the RT-PCR method.

OATP-A
OAA-1 primer
(5' aag aag agg tca aga agg aaa aat 3'/ SEQ ID NO: 29),
and

OAA-2 primer
(5' gga gca tca agg aac agt cag gtc 3'/ SEQ ID NO: 30).

OATP-B
4742-1 primer
(5' cgt gcg gcc aag tgt gtt cca taa 3'/ SEQ ID NO: 31),
and 4742-2 primer
(5' gaa gga gta gcc cca tag cca atc 3'/ SEQ ID NO: 32).

OATP-C
9414-1 primer
(5' tgt cat tgt cct ttt acc tat tat 3'/ SEQ ID NO: 33),
and 9414-2 primer
(above-deseribed, 5' tgt aag tta ttc cat tgt ttc cac 3'/SEQ ID NO: 13).

OATP-D
02242 primer
(5' ctc aaa tcc ttc gcc ttc atc ctg 3'/ SEQ ID NO: 34),
and 02244 primer
(5' agg gtc aga gta gag gca aag aac 3'/ SEQ ID NO: 35).

OATP-E
71302 primer
(5' cac ggc ggg cac tca gca ttt cct 3'/ SEQ ID NO: 36),
and 71304 primer
(above deseribed, 5' cga tcg ggt ata aaa cac att cta 3'/SEQ ID NO: 24).

G3PDH
Upstream primer
(5' TGAAGGTCGGAGTCAACGGATTTGGT 3'/SEQ ID NO: 37),
and

Downstream primer
(5' CATGTGGGCCATGAGGTCCACCAC 3'/SEQ ID NO: 38).

Figure 2:
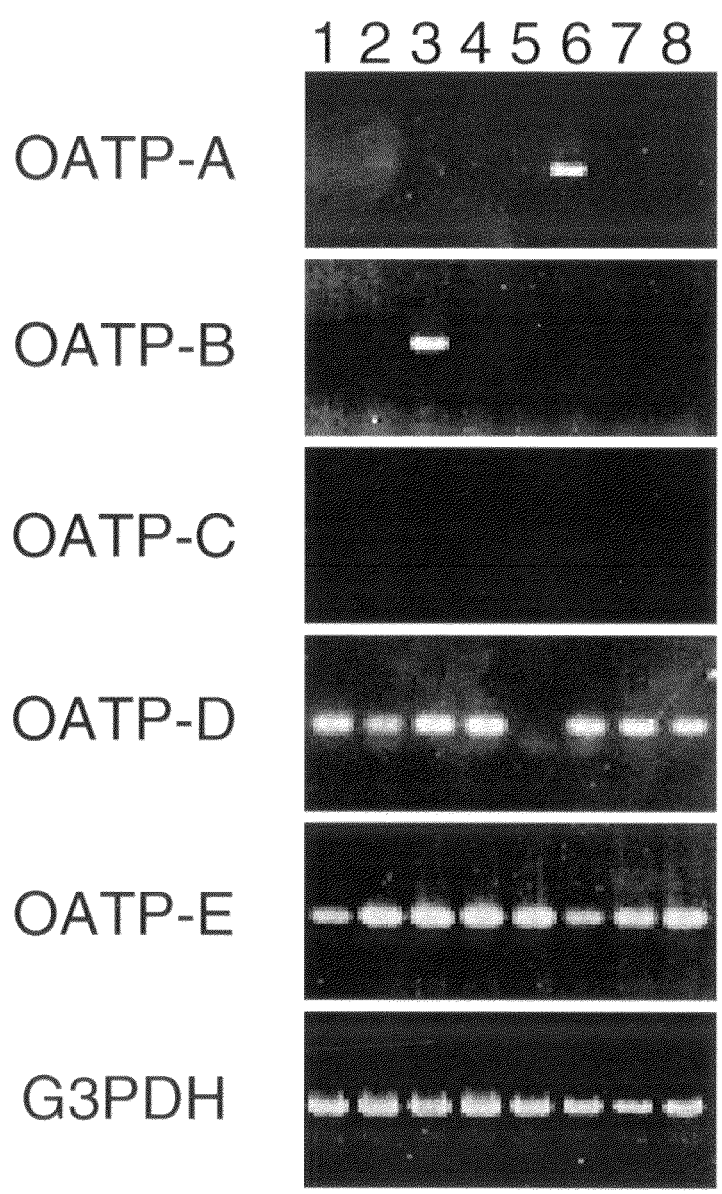
FIG. 2 is a photograph showing the results of examination by the RT-PCR method for the expression level of respective OATP family genes in human cancer cells: 1. mammary cancer cells (GI-101), 2. lung cancer cells (LX-1), 3. large intestinal adenoma cells (CX-1), 4. lung cancer cells (GI-117), 5. prostatic adenoma cells, 6. large intestinal adenoma cells (GI-112), 7. ovary cancer cells (GI-102), and 8. pancreatic adenoma cells (GI-103).

PCR was performed with appropriate amounts of cDNAs derived from various organs and cells contained in the Multiple Tissue cDNA (MTC™) Panel (CLONTECH) as template using the above-described primers. PCR-amplified products were analyzed by agarose electrophoresis (FIGS. 1 and 2). OATP-A showed an expression pattern comparatively restricted in brain and liver. Expression of OATP-C was discovered to be restricted in liver in both fetal and adult tissues examined. Although OATP-B, OATP-D, and OATP-E were found to be expressed in a relatively wide range of tissues, it was revealed that OATP-B and OATP-E, among them, were expressed extremely low in the peripheral blood leukocytes, thymus, and spleen. These findings strongly indicate that expressions of OATP-B and OATP-E are low in hemocytes. On the other hand, the examination of OATPs in cancer cells have revealed that both OATP-D and OATP-E are expressed in a high frequency in these cells (FIG. 2). From these results, the potential production of an anticancer agent which is specifically incorporated into cells by the OATP-E protein is expected, such an agent being an anticancer agent with an attenuated side effects on hematopoietic cells (e.g. bone marrow suppression, and such).

Example 3

Transport Experiment

The human fetal kidney-derived cell strain, HEK 293 cells, were transfected with the plasmid pcDNA3/OATP-C or the pcDNA3 vector containing no insert as a control (mock) by the calcium phosphate method. Specifically, the plasmid DNA (10 μg), a Hepes buffer solution (137 mM NaCl, 5 mM KCl, 0.7 mM $Na_2HPO_4$, 6 mM dextrose, and 21 mM Hepes pH 7.1) (1 ml), and 2 M $CaCl_2$ (62.5 μl) were mixed and the resultant mixture was allowed to stand at room temperature for 30 min or more to form calcium phosphate coprecipitates. After the cells were plated on 10-cm diameter plates at a concentration of $1.5 \times 10^6$ cells per plate, and the cells were cultured for 24 h. The above-described calcium phosphate coprecipitates were added thereto, and the cells were further cultured for 24 h. Then, plates were washed with phosphate buffered saline (PBS), and after the addition of fresh culture medium, the cells were further cultured for 24 h.

Transport experiment was performed using the cells transfected with the plasmid DNA according to the following procedures. The cells were detached from the plates using a rubber policeman, suspended in a transport buffer (containing 125 mM NaCl, 4.8 mM KCl, 5.6 mM (+)-glucose, 1.2 mM $CaCl_2$, 1.2 mM $KH_2PO_4$, 1.2 mM $MgSO_4$, and 25 mM Hepes pH 7.4), and pre-incubated for 20 min. Each of various labeled substrates ([$^3$H]methotrexate, [$^3$H]digoxin, [$^3$H]ouabain, [$^3$H]prostaglandin E2, [$^3$H]estradiol-17β-glucuronide, [$^3$H]estron-3-sulfate, [$^{14}$C]PCG<benzylpenicillin>, and so on) was then added in an appropriate amount to the above-described cell suspension, and the resulting mixture was incubated at 37° C. for a predetermined period of time. Incubated cells were overlaid on a silicon layer formed by laying a mixture of silicon oil and liquid paraffin (specific gravity=1.022) on a 3 M KCl layer, and separated by centrifugation. Radioactivity of cells was measured to determine the into-the-cell transport activity. In this case, $1 \times 10^6$ cells were used as one point of cells.

Herein, the culture of HEK 293 cells was performed using Dulbecco's MEM containing 10% FCS (fetal calf serum) as the culture medium in an atmosphere of 5% carbon dioxide at 37° C.

Figure 3:
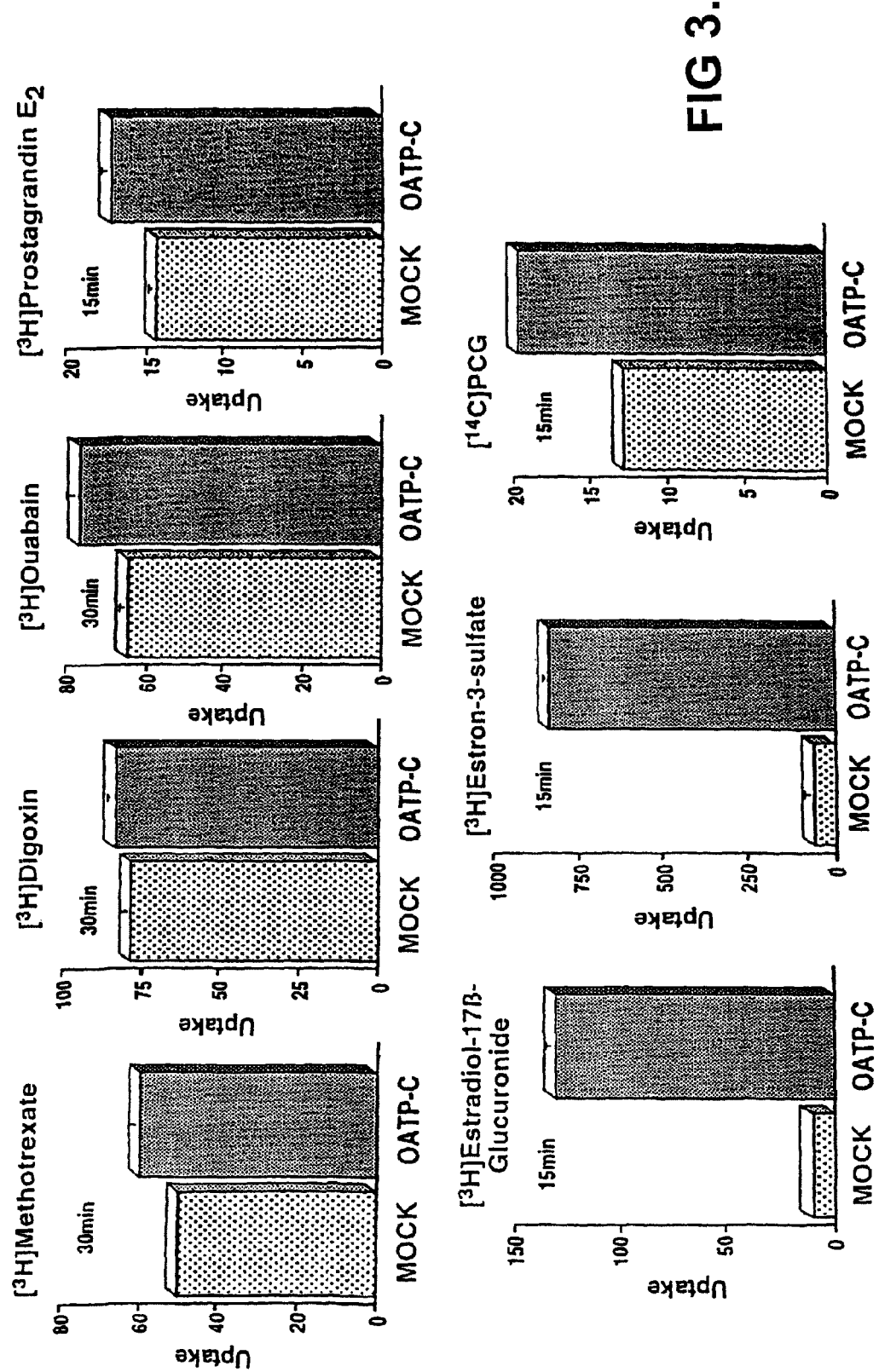
FIG. 3 is a bar graph showing the results of transport experiments for various labeled compounds. More particularly, the transport activities for various labeled compounds of HEK293 cells transfected with OATP-C (OATP-C) or with the vector alone (mock) are shown.

From measuring the transport activity in HEK293 cells wherein the OATP-C proteins had been expressed, transport was obviously observed with estradiol-17β-glucuronide, estron-3-sulfate, and PCG. A weak transport activity was also observed with methotrexate, ouabain, and prostaglandin E2 (FIG. 3).

Figure 4:
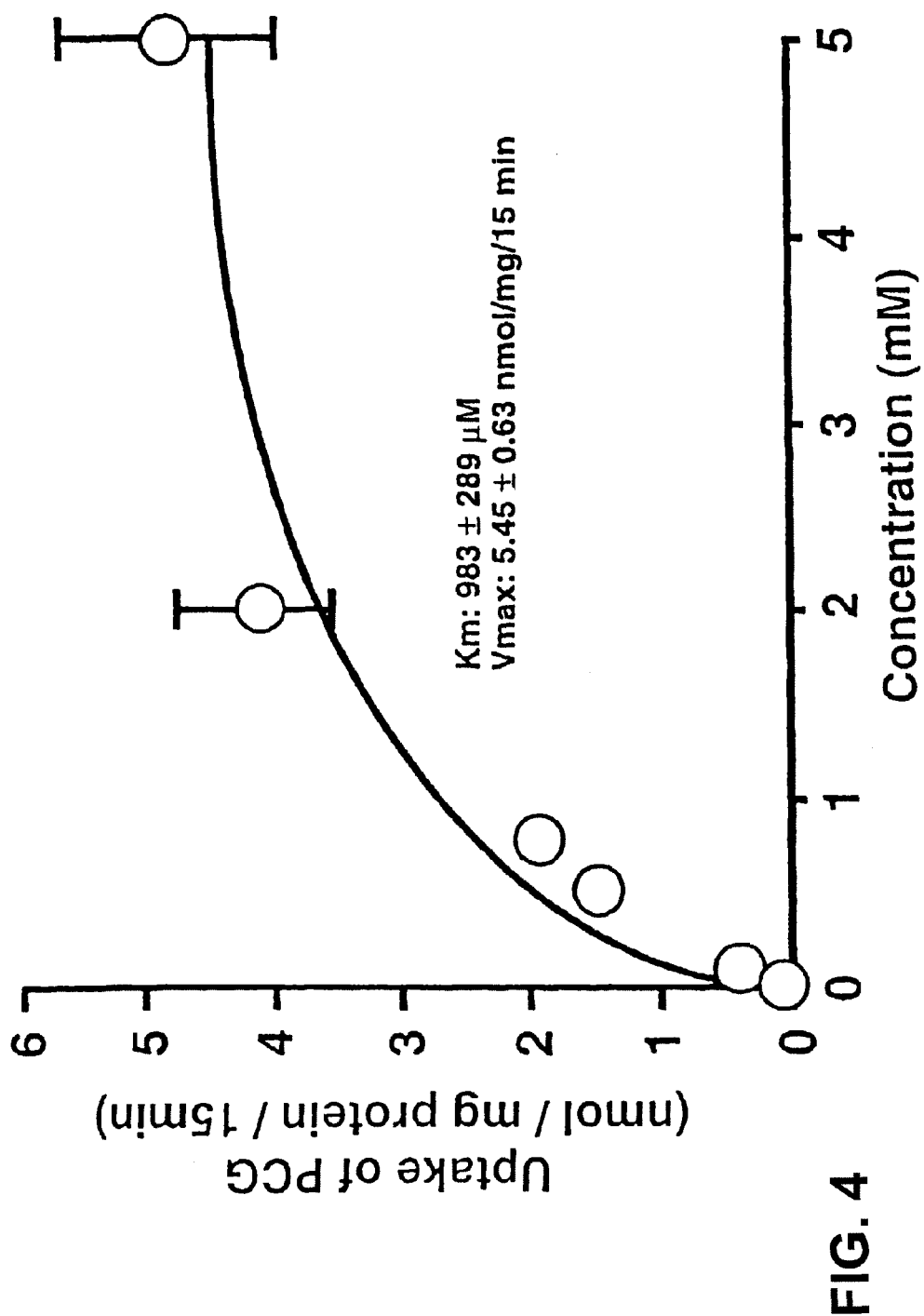
FIG. 4 is a graph showing the concentration-dependency of the transport activity for PCG of HEK293 cells expressing the OATP-C protein.

Further, to obtain the Km (Michaelis constant) value of the PCG transport mediated by the OATP-C protein, the uptake of [$^{14}$C]PCG added at various concentrations was measured (FIG. 4). From the Lineweaver-Burk reciprocal plot of the net PCG uptake obtained in the cells wherein the OATP-C proteins are expressed, a Km value of 983±289 μM PCG was obtained with a maximal velocity Vmax of 5.45±0.63 (nmol/mg/15 min).

Figure 5:
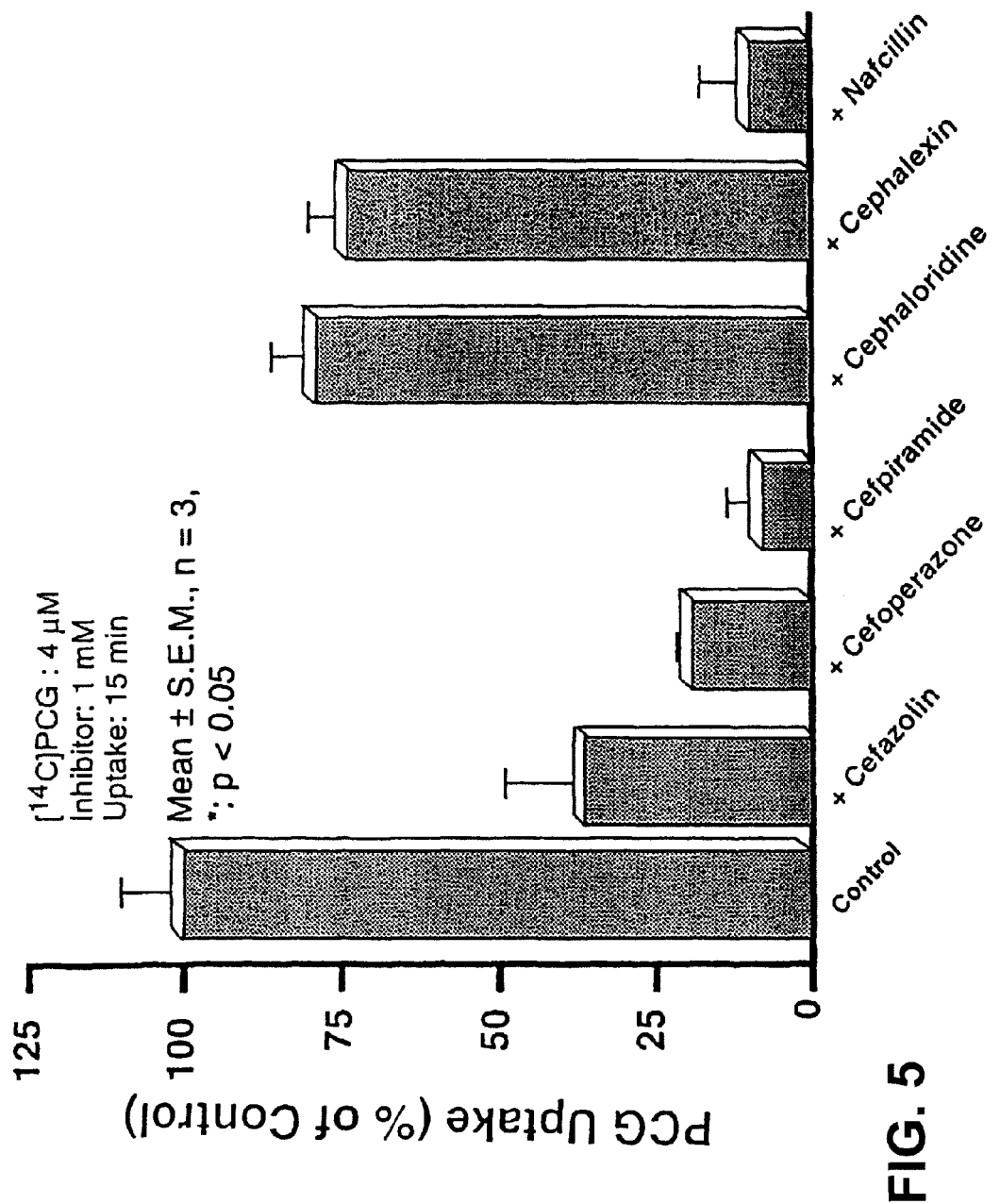
FIG. 5 is a bar graph showing the effect of various β-lactam antibiotics on the transport activity for PCG in HEK293 cells wherein the OATP-C protein is expressed. The transport activity in the control (with no inhibitor) is taken as 100%.

Furthermore, the effects of the addition of various β-lactam antibiotics on the PCG transport mediated by the OATP-C protein were examined (FIG. 5). Remarkable inhibitory activity was observed with cefazolin, cefoperazone, cefpiramide, and nafcillin when effects of various β-lactam antibiotics were examined by adding them at a concentration of 1 mM, respectively, to the transport activity of 4 μM [$^{14}$C]PCG. A weak inhibitory activity was also seen with cefaloridine and cefalexin. These results strongly indicate that these β-lactam antibiotics can be also transported by the OATP family proteins similarly as PCG belonging to the same β-lactam antibiotics.

Figure 6:
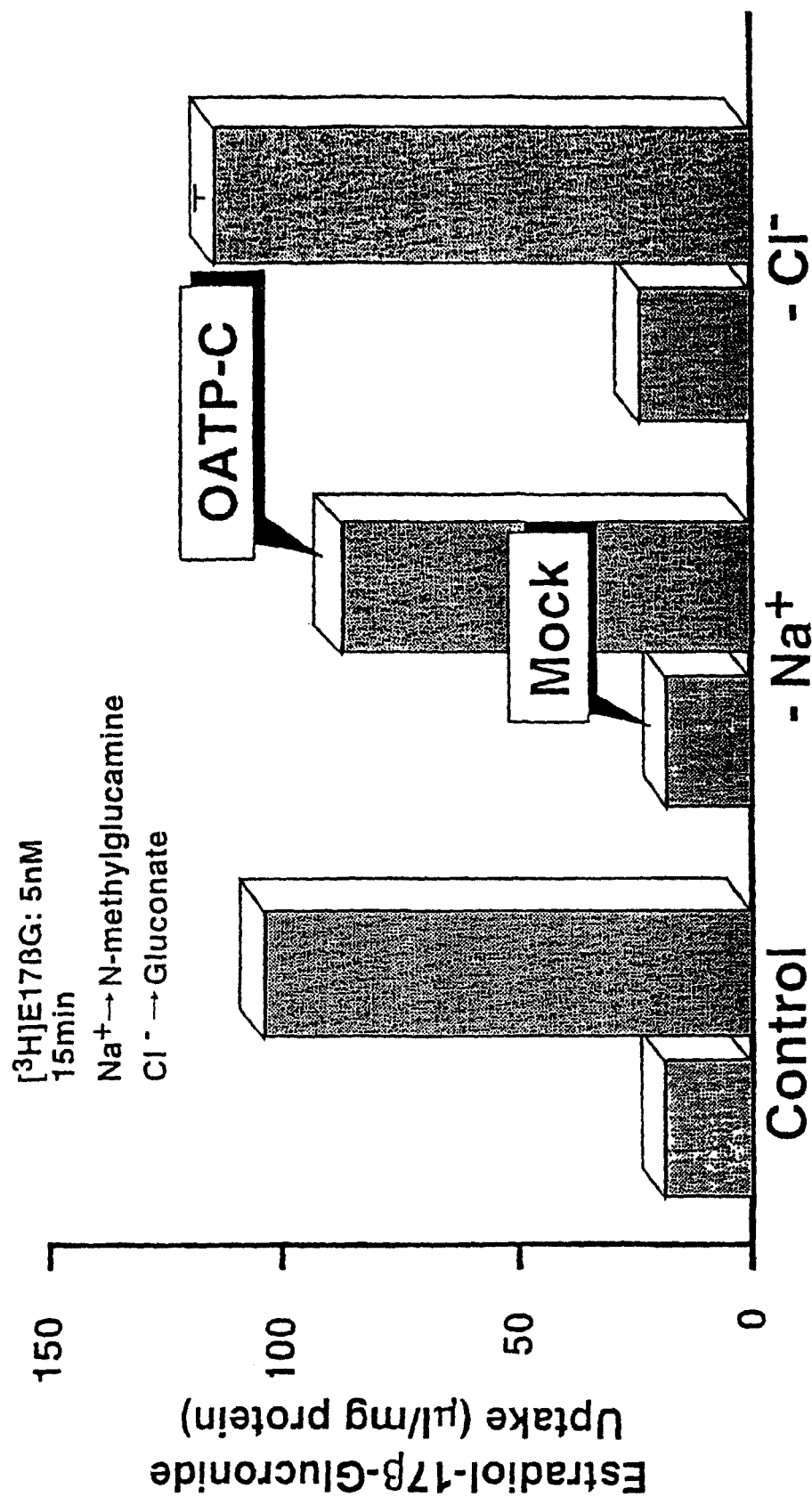
FIG. 6 is a bar graph showing the sodium ion and chloride ion dependencies of the transport activity for estradiol-17β-glucuronide. "OATP-C" represents the transport activity for estradiol-17β-glucuronide of HEK293 cells transfected with OATP-C, and "Mock" represents the transport activity for estradiol-17β-glucuronide of HEK293 cells transfected with the vector alone.

Further, the requirement for sodium and chloride ions in the transport of estradiol-17β-glucuronide mediated by the OATP-C protein was examined (FIG. 6). No alteration was observed in the transport of estradiol-17β-glucuronide either in case where the sodium ion was replaced with N-methyl-glucamine, or where the chloride ion was substituted with gluconate. According to these results, it has been revealed that the transport mediated by the OATP-C protein is independent to sodium ion.

INDUSTRIAL APPLICABILITY

The present invention provides novel transporter proteins and genes encoding these proteins. These proteins and genes are useful for developing drugs with a new design that can be transported by transporter proteins of this invention, and pharmaceuticals for the treatment of disorders caused by expressional and functional aberrations of these transporter proteins. Furthermore, these proteins and genes can be applied to genetic diagnosis and gene therapy. For example, by the SNP diagnosis and such of transporter genes of this invention, it is possible to design a tailor-made treatment plan, taking individual differences in efficacy of drugs into consideration.

We claim:

1. An isolated nucleic acid of any one of (a) to (d) below:
   (a) a cDNA encoding a protein comprising the amino acid sequence of SEQ ID NO: 6;
   (b) a cDNA comprising the coding region consisting of nucleotides 1-2130 of the nucleotide sequence of SEQ ID NO: 5;
   (c) a cDNA comprising the nucleotide sequence of SEQ ID NO: 5; and
   (d) a cDNA consisting of the nucleotide sequence of SEQ ID NO: 5.

2. The isolated nucleic acid of claim 1, comprising the cDNA encoding a protein comprising the amino acid sequence of SEQ ID NO: 6.

3. The isolated nucleic acid of claim 1, comprising the cDNA consisting of the nucleotide sequence of SEQ ID NO: 5.

4. A cDNA encoding the amino acid sequence of SEQ ID NO: 6.

5. A vector into which the nucleic acid of claim 1 is inserted.

6. A vector into which the nucleic acid of claim 4 is inserted.

7. An isolated cell in culture comprising the vector of claim 5.

8. An isolated cell in culture comprising the vector of claim 6.

9. A method for producing a polypeptide, the method comprising the steps of:
   culturing an isolated cell comprising a vector into which the nucleic acid of claim 1 is inserted; and
   recovering the polypeptide that is encoded by the nucleic acid and expressed from the isolated cell or the culture supernatant thereof.

10. A method for producing a polypeptide, the method comprising the steps of:
    (a) culturing an isolated cell comprising a vector into which the nucleic acid of claim 4 is inserted; and
    (b) recovering the polypeptide that is encoded by the nucleic acid and expressed from the isolated cell or the culture supernatant thereof.

* * * * *

SEQUENCE LISTING

<160> NUMBER OF SEQ ID NOS: 38

<210> SEQ ID NO 1
<211> LENGTH: 2354
<212> TYPE: DNA
<213> ORGANISM: Homo sapiens

```
<220> FEATURE:
<221> NAME/KEY: CDS
<222> LOCATION: (179)..(2305)

<400> SEQUENCE: 1
ctgtgtggcc caagaagaac tgaccccgtg tctggagctc ccaccgttat tgcatccctg      60
ctgtggctca cctgctgctg tctccaggag cccctgagaa gatttgcctc ctctcccctg     120
ctaagctcca ggtcctgaga ttgaattagg ggctggagct cactgcactc cagcagtc      178 atg gga ccc agg ata ggg cca gcg ggt gag gta ccc cag gta cca gac      226
Met Gly Pro Arg Ile Gly Pro Ala Gly Glu Val Pro Gln Val Pro Asp
  1               5                  10                  15 aag gaa acc aaa gcc aca atg ggc aca gaa aac aca cct gga ggc aaa      274
Lys Glu Thr Lys Ala Thr Met Gly Thr Glu Asn Thr Pro Gly Gly Lys
             20                  25                  30 gcc agc cca gac cct cag gac gtg cgg cca agt gtg ttc cat aac atc      322
Ala Ser Pro Asp Pro Gln Asp Val Arg Pro Ser Val Phe His Asn Ile
         35                  40                  45 aag ctg ttc gtt ctg tgc cac agc ctg ctg cag ctg gcg cag ctc atg      370
Lys Leu Phe Val Leu Cys His Ser Leu Leu Gln Leu Ala Gln Leu Met
     50                  55                  60 atc tcc ggc tac cta aag agc tcc atc tcc aca gtg gag aag cgc ttc      418
Ile Ser Gly Tyr Leu Lys Ser Ser Ile Ser Thr Val Glu Lys Arg Phe
 65                  70                  75                  80 ggc ctc tcc agc cag acg tcg ggg ctg ctg gcc tcc ttc aac gag gtg      466
Gly Leu Ser Ser Gln Thr Ser Gly Leu Leu Ala Ser Phe Asn Glu Val
                 85                  90                  95 ggg aac aca gcc ttg att gtg ttt gtg agc tat ttt ggc agc cgg gtg      514
Gly Asn Thr Ala Leu Ile Val Phe Val Ser Tyr Phe Gly Ser Arg Val
                100                 105                 110 cac cga ccc cga atg att ggc tat ggg gct atc ctt gtg gcc ctg gcg      562
His Arg Pro Arg Met Ile Gly Tyr Gly Ala Ile Leu Val Ala Leu Ala
            115                 120                 125 ggc ctg ctc atg act ctc ccg cac ttc atc tcg gag cca tac cgc tac      610
Gly Leu Leu Met Thr Leu Pro His Phe Ile Ser Glu Pro Tyr Arg Tyr
        130                 135                 140 gac aac acc agc cct gag gat atg cca cag gac ttc aag gct tcc ctg      658
Asp Asn Thr Ser Pro Glu Asp Met Pro Gln Asp Phe Lys Ala Ser Leu
145                 150                 155                 160 tgc ctg ccc aca acc tcg gcc cca gcc tcg gcc ccc tcc aat ggc aac      706
Cys Leu Pro Thr Thr Ser Ala Pro Ala Ser Ala Pro Ser Asn Gly Asn
                165                 170                 175 tgc tca agc tac aca gaa acc cag cat ctg agt gtg gtg ggg atc atg      754
Cys Ser Ser Tyr Thr Glu Thr Gln His Leu Ser Val Val Gly Ile Met
            180                 185                 190 ttc gtg gca cag acc ctg ctg ggc gtg ggc ggg gtg ccc att cag ccc      802
Phe Val Ala Gln Thr Leu Leu Gly Val Gly Gly Val Pro Ile Gln Pro
        195                 200                 205 ttt ggc atc tcc tac atc gat gac ttt gcc cac aac agc aac tcg ccc      850
Phe Gly Ile Ser Tyr Ile Asp Asp Phe Ala His Asn Ser Asn Ser Pro
    210                 215                 220 ctc tac ctc ggg atc ctg ttt gca gtg acc atg atg ggg cca ggc ctg      898
Leu Tyr Leu Gly Ile Leu Phe Ala Val Thr Met Met Gly Pro Gly Leu
225                 230                 235                 240 gcc ttt ggg ctg ggc agc ctc atg ctg cgc ctt tat gtg gac att aac      946
Ala Phe Gly Leu Gly Ser Leu Met Leu Arg Leu Tyr Val Asp Ile Asn
                245                 250                 255 cag atg cca gaa ggt ggt atc agc ctg acc ata aag gac ccc cga tgg      994
Gln Met Pro Glu Gly Gly Ile Ser Leu Thr Ile Lys Asp Pro Arg Trp
            260                 265                 270
```

-continued

| | | | | | | | | | | | | | | | | |
|---|---|---|---|---|---|---|---|---|---|---|---|---|---|---|---|---|
| gtg | ggt | gcc | tgg | tgg | ctg | ggt | ttc | ctc | atc | gct | gcc | ggt | gca | gtg | gcc | 1042 |
| Val | Gly | Ala | Trp | Trp | Leu | Gly | Phe | Leu | Ile | Ala | Ala | Gly | Ala | Val | Ala | |
| | | 275 | | | | 280 | | | | | 285 | | | | | |
| ctg | gct | gcc | atc | ccc | tac | ttc | ttc | ttc | ccc | aag | gaa | atg | ccc | aag | gaa | 1090 |
| Leu | Ala | Ala | Ile | Pro | Tyr | Phe | Phe | Phe | Pro | Lys | Glu | Met | Pro | Lys | Glu | |
| | 290 | | | | | 295 | | | | | 300 | | | | | |
| aaa | cgt | gag | ctt | cag | ttt | cgg | cga | aag | gtc | tta | gca | gtc | aca | gac | tca | 1138 |
| Lys | Arg | Glu | Leu | Gln | Phe | Arg | Arg | Lys | Val | Leu | Ala | Val | Thr | Asp | Ser | |
| 305 | | | | | 310 | | | | | 315 | | | | | 320 | |
| cct | gcc | agg | aag | ggc | aag | gac | tct | ccc | tct | aag | cag | agc | cct | ggg | gag | 1186 |
| Pro | Ala | Arg | Lys | Gly | Lys | Asp | Ser | Pro | Ser | Lys | Gln | Ser | Pro | Gly | Glu | |
| | | | | 325 | | | | | 330 | | | | | 335 | | |
| tcc | acg | aag | aag | cag | gat | ggc | cta | gtc | cag | att | gca | cca | aac | ctg | act | 1234 |
| Ser | Thr | Lys | Lys | Gln | Asp | Gly | Leu | Val | Gln | Ile | Ala | Pro | Asn | Leu | Thr | |
| | | | 340 | | | | | 345 | | | | | 350 | | | |
| gtg | atc | cag | ttc | att | aaa | gtc | ttc | ccc | agg | gtg | ctg | ctg | cag | acc | cta | 1282 |
| Val | Ile | Gln | Phe | Ile | Lys | Val | Phe | Pro | Arg | Val | Leu | Leu | Gln | Thr | Leu | |
| | | 355 | | | | | 360 | | | | | 365 | | | | |
| cgc | cac | ccc | atc | ttc | ctg | ctg | gtg | gtc | ctg | tcc | cag | gta | tgc | ttg | tca | 1330 |
| Arg | His | Pro | Ile | Phe | Leu | Leu | Val | Val | Leu | Ser | Gln | Val | Cys | Leu | Ser | |
| | 370 | | | | | 375 | | | | | 380 | | | | | |
| tcc | atg | gct | gcg | ggc | atg | gcc | acc | ttc | ctg | ccc | aag | ttc | ctg | gag | cgc | 1378 |
| Ser | Met | Ala | Ala | Gly | Met | Ala | Thr | Phe | Leu | Pro | Lys | Phe | Leu | Glu | Arg | |
| 385 | | | | | 390 | | | | | 395 | | | | | 400 | |
| cag | ttt | tcc | atc | aca | gcc | tcc | tac | gcc | aac | ctg | ctc | atc | ggc | tgc | ctc | 1426 |
| Gln | Phe | Ser | Ile | Thr | Ala | Ser | Tyr | Ala | Asn | Leu | Leu | Ile | Gly | Cys | Leu | |
| | | | | 405 | | | | | 410 | | | | | 415 | | |
| tcc | ttc | cct | tcg | gtc | atc | gtg | ggc | atc | gtg | gtg | ggt | ggc | gtc | ctg | gtc | 1474 |
| Ser | Phe | Pro | Ser | Val | Ile | Val | Gly | Ile | Val | Val | Gly | Gly | Val | Leu | Val | |
| | | | | 420 | | | | | 425 | | | | | 430 | | |
| aag | cgg | ctc | cac | ctg | ggc | cct | gtg | gga | tgc | ggt | gcc | ctt | tgc | ctg | ctg | 1522 |
| Lys | Arg | Leu | His | Leu | Gly | Pro | Val | Gly | Cys | Gly | Ala | Leu | Cys | Leu | Leu | |
| | | | 435 | | | | | 440 | | | | | 445 | | | |
| ggg | atg | ctg | ctg | tgc | ctc | ttc | ttc | agc | ctg | ccg | ctc | ttc | ttt | atc | ggc | 1570 |
| Gly | Met | Leu | Leu | Cys | Leu | Phe | Phe | Ser | Leu | Pro | Leu | Phe | Phe | Ile | Gly | |
| | | | 450 | | | | | 455 | | | | | 460 | | | |
| tgc | tcc | agc | cac | cag | att | gcg | ggc | atc | aca | cac | cag | acc | agt | gcc | cac | 1618 |
| Cys | Ser | Ser | His | Gln | Ile | Ala | Gly | Ile | Thr | His | Gln | Thr | Ser | Ala | His | |
| 465 | | | | | 470 | | | | | 475 | | | | | 480 | |
| cct | ggg | ctg | gag | ctg | tct | cca | agc | tgc | atg | gag | gcc | tgc | tcc | tgc | cca | 1666 |
| Pro | Gly | Leu | Glu | Leu | Ser | Pro | Ser | Cys | Met | Glu | Ala | Cys | Ser | Cys | Pro | |
| | | | | 485 | | | | | 490 | | | | | 495 | | |
| ttg | gac | ggc | ttt | aac | cct | gtc | tgc | gac | ccc | agc | act | cgt | gtg | gaa | tac | 1714 |
| Leu | Asp | Gly | Phe | Asn | Pro | Val | Cys | Asp | Pro | Ser | Thr | Arg | Val | Glu | Tyr | |
| | | | 500 | | | | | 505 | | | | | 510 | | | |
| atc | aca | ccc | tgc | cac | gca | ggc | tgc | tca | agc | tgg | gtg | gtc | cag | gat | gct | 1762 |
| Ile | Thr | Pro | Cys | His | Ala | Gly | Cys | Ser | Ser | Trp | Val | Val | Gln | Asp | Ala | |
| | | 515 | | | | | 520 | | | | | 525 | | | | |
| ctg | gac | aac | agc | cag | gtt | ttc | tac | acc | aac | tgc | agc | tgc | gtg | gtg | gag | 1810 |
| Leu | Asp | Asn | Ser | Gln | Val | Phe | Tyr | Thr | Asn | Cys | Ser | Cys | Val | Val | Glu | |
| | 530 | | | | | 535 | | | | | 540 | | | | | |
| ggc | aac | ccc | gtg | ctg | gca | gga | tcc | tgc | gac | tca | acg | tgc | agc | cat | ctg | 1858 |
| Gly | Asn | Pro | Val | Leu | Ala | Gly | Ser | Cys | Asp | Ser | Thr | Cys | Ser | His | Leu | |
| 545 | | | | | 550 | | | | | 555 | | | | | 560 | |
| gtg | gtg | ccc | ttc | ctg | ctc | ctg | gtc | agc | ctg | ggc | tcg | gcc | ctg | gcc | tgt | 1906 |
| Val | Val | Pro | Phe | Leu | Leu | Leu | Val | Ser | Leu | Gly | Ser | Ala | Leu | Ala | Cys | |
| | | | | 565 | | | | | 570 | | | | | 575 | | |
| ctc | acc | cac | aca | ccc | tcc | ttc | atg | ctc | atc | cta | aga | gga | gtg | aag | aaa | 1954 |
| Leu | Thr | His | Thr | Pro | Ser | Phe | Met | Leu | Ile | Leu | Arg | Gly | Val | Lys | Lys | |
| | | | 580 | | | | | 585 | | | | | 590 | | | |

```
gaa gac aag act ttg gct gtg ggc atc cag ttc atg ttc ctg agg att    2002
Glu Asp Lys Thr Leu Ala Val Gly Ile Gln Phe Met Phe Leu Arg Ile
        595                 600                 605 ttg gcc tgg atg ccc agc ccc gtg atc cac ggc agc gcc atc gac acc    2050
Leu Ala Trp Met Pro Ser Pro Val Ile His Gly Ser Ala Ile Asp Thr
    610                 615                 620 acc tgt gtg cac tgg gcc ctg agc tgt ggg cgt cga gct gtc tgt cgc    2098
Thr Cys Val His Trp Ala Leu Ser Cys Gly Arg Arg Ala Val Cys Arg
625                 630                 635                 640 tac tac aat aat gac ctg ctc cga aac cgg ttc atc ggc ctc cag ttc    2146
Tyr Tyr Asn Asn Asp Leu Leu Arg Asn Arg Phe Ile Gly Leu Gln Phe
                645                 650                 655 ttc ttc aaa aca ggt tct gtg atc tgc ttc gcc tta gtt ttg gct gtc    2194
Phe Phe Lys Thr Gly Ser Val Ile Cys Phe Ala Leu Val Leu Ala Val
            660                 665                 670 ctg agg cag cag gac aaa gag gca agg acc aaa gag agc aga tcc agc    2242
Leu Arg Gln Gln Asp Lys Glu Ala Arg Thr Lys Glu Ser Arg Ser Ser
        675                 680                 685 cct gcc gta gag cag caa ttg cta gtg tcg ggg cca ggg aag aag cca    2290
Pro Ala Val Glu Gln Gln Leu Leu Val Ser Gly Pro Gly Lys Lys Pro
    690                 695                 700 gag gat tcc cga gtg tgagctgtct tggggcccca cctggccaag agtagcagcc    2345
Glu Asp Ser Arg Val
705 acagcagta                                                          2354

<210> SEQ ID NO 2
<211> LENGTH: 709
<212> TYPE: PRT
<213> ORGANISM: Homo sapiens

<400> SEQUENCE: 2

Met Gly Pro Arg Ile Gly Pro Ala Gly Glu Val Pro Gln Val Pro Asp
  1               5                  10                  15

Lys Glu Thr Lys Ala Thr Met Gly Thr Glu Asn Thr Pro Gly Gly Lys
             20                  25                  30

Ala Ser Pro Asp Pro Gln Asp Val Arg Pro Ser Val Phe His Asn Ile
         35                  40                  45

Lys Leu Phe Val Leu Cys His Ser Leu Leu Gln Leu Ala Gln Leu Met
     50                  55                  60

Ile Ser Gly Tyr Leu Lys Ser Ser Ile Ser Thr Val Glu Lys Arg Phe
 65                  70                  75                  80

Gly Leu Ser Ser Gln Thr Ser Gly Leu Leu Ala Ser Phe Asn Glu Val
                 85                  90                  95

Gly Asn Thr Ala Leu Ile Val Phe Val Ser Tyr Phe Gly Ser Arg Val
            100                 105                 110

His Arg Pro Arg Met Ile Gly Tyr Gly Ala Ile Leu Val Ala Leu Ala
        115                 120                 125

Gly Leu Leu Met Thr Leu Pro His Phe Ile Ser Glu Pro Tyr Arg Tyr
    130                 135                 140

Asp Asn Thr Ser Pro Glu Asp Met Pro Gln Asp Phe Lys Ala Ser Leu
145                 150                 155                 160

Cys Leu Pro Thr Thr Ser Ala Pro Ala Ser Ala Pro Ser Asn Gly Asn
                165                 170                 175

Cys Ser Ser Tyr Thr Glu Thr Gln His Leu Ser Val Val Gly Ile Met
            180                 185                 190

Phe Val Ala Gln Thr Leu Leu Gly Val Gly Gly Val Pro Ile Gln Pro
        195                 200                 205
```

-continued

```
Phe Gly Ile Ser Tyr Ile Asp Asp Phe Ala His Asn Ser Asn Ser Pro
    210                 215                 220
Leu Tyr Leu Gly Ile Leu Phe Ala Val Thr Met Met Gly Pro Gly Leu
225                 230                 235                 240
Ala Phe Gly Leu Gly Ser Leu Met Leu Arg Leu Tyr Val Asp Ile Asn
                245                 250                 255
Gln Met Pro Glu Gly Ile Ser Leu Thr Ile Lys Asp Pro Arg Trp
            260                 265                 270
Val Gly Ala Trp Trp Leu Gly Phe Leu Ile Ala Ala Gly Ala Val Ala
            275                 280                 285
Leu Ala Ala Ile Pro Tyr Phe Phe Pro Lys Glu Met Pro Lys Glu
    290                 295                 300
Lys Arg Glu Leu Gln Phe Arg Arg Lys Val Leu Ala Val Thr Asp Ser
305                 310                 315                 320
Pro Ala Arg Lys Gly Lys Asp Ser Pro Ser Lys Gln Ser Pro Gly Glu
                325                 330                 335
Ser Thr Lys Lys Gln Asp Gly Leu Val Gln Ile Ala Pro Asn Leu Thr
                340                 345                 350
Val Ile Gln Phe Ile Lys Val Phe Pro Arg Val Leu Leu Gln Thr Leu
                355                 360                 365
Arg His Pro Ile Phe Leu Leu Val Val Leu Ser Gln Val Cys Leu Ser
    370                 375                 380
Ser Met Ala Ala Gly Met Ala Thr Phe Leu Pro Lys Phe Leu Glu Arg
385                 390                 395                 400
Gln Phe Ser Ile Thr Ala Ser Tyr Ala Asn Leu Leu Ile Gly Cys Leu
                405                 410                 415
Ser Phe Pro Ser Val Ile Val Gly Ile Val Gly Gly Val Leu Val
                420                 425                 430
Lys Arg Leu His Leu Gly Pro Val Gly Cys Gly Ala Leu Cys Leu Leu
                435                 440                 445
Gly Met Leu Leu Cys Leu Phe Phe Ser Leu Pro Leu Phe Phe Ile Gly
    450                 455                 460
Cys Ser Ser His Gln Ile Ala Gly Ile Thr His Gln Thr Ser Ala His
465                 470                 475                 480
Pro Gly Leu Glu Leu Ser Pro Ser Cys Met Glu Ala Cys Ser Cys Pro
                485                 490                 495
Leu Asp Gly Phe Asn Pro Val Cys Asp Pro Ser Thr Arg Val Glu Tyr
                500                 505                 510
Ile Thr Pro Cys His Ala Gly Cys Ser Ser Trp Val Val Gln Asp Ala
    515                 520                 525
Leu Asp Asn Ser Gln Val Phe Tyr Thr Asn Cys Ser Cys Val Val Glu
    530                 535                 540
Gly Asn Pro Val Leu Ala Gly Ser Cys Asp Ser Thr Cys Ser His Leu
545                 550                 555                 560
Val Val Pro Phe Leu Leu Leu Val Ser Leu Gly Ser Ala Leu Ala Cys
                565                 570                 575
Leu Thr His Thr Pro Ser Phe Met Leu Ile Leu Arg Gly Val Lys Lys
    580                 585                 590
Glu Asp Lys Thr Leu Ala Val Gly Ile Gln Phe Met Phe Leu Arg Ile
            595                 600                 605
Leu Ala Trp Met Pro Ser Pro Val Ile His Gly Ser Ala Ile Asp Thr
    610                 615                 620
Thr Cys Val His Trp Ala Leu Ser Cys Gly Arg Arg Ala Val Cys Arg
```

```
                625                 630                 635                 640
Tyr Tyr Asn Asn Asp Leu Leu Arg Asn Arg Phe Ile Gly Leu Gln Phe
                            645                 650                 655

Phe Phe Lys Thr Gly Ser Val Ile Cys Phe Ala Leu Val Leu Ala Val
            660                 665                 670

Leu Arg Gln Gln Asp Lys Glu Ala Arg Thr Lys Glu Ser Arg Ser Ser
        675                 680                 685

Pro Ala Val Glu Gln Gln Leu Leu Val Ser Gly Pro Gly Lys Lys Pro
    690                 695                 700

Glu Asp Ser Arg Val
705

<210> SEQ ID NO 3
<211> LENGTH: 2452
<212> TYPE: DNA
<213> ORGANISM: Homo sapiens
<220> FEATURE:
<221> NAME/KEY: CDS
<222> LOCATION: (100)..(2172)

<400> SEQUENCE: 3
gtggacttgt tgcagttgct gtaggattct aaatccaggt gattgtttca aactgagcat        60
caacaacaaa aacatttgta tgatatctat atttcaatc atg gac caa aat caa       114
                                             Met Asp Gln Asn Gln
                                               1               5 cat ttg aat aaa aca gca gag gca caa cct tca gag aat aag aaa aca       162
His Leu Asn Lys Thr Ala Glu Ala Gln Pro Ser Glu Asn Lys Lys Thr
             10                  15                  20 aga tac tgc aat gga ttg aag atg ttc ttg gca gct ctg tca ctc agc       210
Arg Tyr Cys Asn Gly Leu Lys Met Phe Leu Ala Ala Leu Ser Leu Ser
         25                  30                  35 ttt att gct aag aca cta ggt gca att att atg aaa agt tcc atc att       258
Phe Ile Ala Lys Thr Leu Gly Ala Ile Ile Met Lys Ser Ser Ile Ile
     40                  45                  50 cat ata gaa cgg aga ttt gag ata tcc tct tct ctt gtt ggt ttt att       306
His Ile Glu Arg Arg Phe Glu Ile Ser Ser Ser Leu Val Gly Phe Ile
 55                  60                  65 gac gga agc ttt gaa att gga aat ttg ctt gtg att gta ttt gtg agt       354
Asp Gly Ser Phe Glu Ile Gly Asn Leu Leu Val Ile Val Phe Val Ser
 70                  75                  80                  85 tac ttt gga tcc aaa cta cat aga cca aag tta att gga atc ggt tgt       402
Tyr Phe Gly Ser Lys Leu His Arg Pro Lys Leu Ile Gly Ile Gly Cys
             90                  95                 100 ttc att atg gga att gga ggt gtt ttg act gct ttg cca cat ttc ttc       450
Phe Ile Met Gly Ile Gly Gly Val Leu Thr Ala Leu Pro His Phe Phe
        105                 110                 115 atg gga tat tac agg tat tct aaa gaa act aat atc aat tca tca gaa       498
Met Gly Tyr Tyr Arg Tyr Ser Lys Glu Thr Asn Ile Asn Ser Ser Glu
    120                 125                 130 aat tca aca tcg acc tta tcc act tgt tta att aat caa att tta tca       546
Asn Ser Thr Ser Thr Leu Ser Thr Cys Leu Ile Asn Gln Ile Leu Ser
135                 140                 145 ctc aat aga gca tca cct gag ata gtg gga aaa ggt tgt tta aag gaa       594
Leu Asn Arg Ala Ser Pro Glu Ile Val Gly Lys Gly Cys Leu Lys Glu
150                 155                 160                 165 tct ggg tca tac atg tgg ata tat gtg ttc atg ggt aat atg ctt cgt       642
Ser Gly Ser Tyr Met Trp Ile Tyr Val Phe Met Gly Asn Met Leu Arg
            170                 175                 180 gga ata ggg gag act ccc ata gta cca ctg ggg ctt tct tac att gat       690
Gly Ile Gly Glu Thr Pro Ile Val Pro Leu Gly Leu Ser Tyr Ile Asp
```

```
                185                 190                 195
gat ttc gct aaa gaa gga cat tct tct ttg tat tta ggt ata ttg aat    738
Asp Phe Ala Lys Glu Gly His Ser Ser Leu Tyr Leu Gly Ile Leu Asn
        200                 205                 210 gca ata gca atg att ggt cca atc att ggc ttt acc ctg gga tct ctg    786
Ala Ile Ala Met Ile Gly Pro Ile Ile Gly Phe Thr Leu Gly Ser Leu
215                 220                 225 ttt tct aaa atg tac gtg gat att gga tat gta gat cta agc act atc    834
Phe Ser Lys Met Tyr Val Asp Ile Gly Tyr Val Asp Leu Ser Thr Ile
230                 235                 240                 245 agg ata act cct act gat tct cga tgg gtt gga gct tgg tgg ctt aat    882
Arg Ile Thr Pro Thr Asp Ser Arg Trp Val Gly Ala Trp Trp Leu Asn
            250                 255                 260 ttc ctt gtg tct gga cta ttc tcc att att tct tcc ata cca ttc ttt    930
Phe Leu Val Ser Gly Leu Phe Ser Ile Ile Ser Ser Ile Pro Phe Phe
                265                 270                 275 ttc ttg ccc caa act cca aat aaa cca caa aaa gaa aga aaa gct tca    978
Phe Leu Pro Gln Thr Pro Asn Lys Pro Gln Lys Glu Arg Lys Ala Ser
            280                 285                 290 ctg tct ttg cat gtg ctg gaa aca aat gat gaa aag gat caa aca gct   1026
Leu Ser Leu His Val Leu Glu Thr Asn Asp Glu Lys Asp Gln Thr Ala
295                 300                 305 aat ttg acc aat caa gga aaa aat att acc aaa aat gtg act ggt ttt   1074
Asn Leu Thr Asn Gln Gly Lys Asn Ile Thr Lys Asn Val Thr Gly Phe
310                 315                 320                 325 ttc cag tct ttt aaa agc atc ctt act aat ccc ctg tat gtt atg ttt   1122
Phe Gln Ser Phe Lys Ser Ile Leu Thr Asn Pro Leu Tyr Val Met Phe
                330                 335                 340 gtg ctt ttg acg ttg tta caa gta agc agc tat att ggt gct ttt act   1170
Val Leu Leu Thr Leu Leu Gln Val Ser Ser Tyr Ile Gly Ala Phe Thr
            345                 350                 355 tat gtc ttc aaa tac gta gag caa cag tat ggt cag cct tca tct aag   1218
Tyr Val Phe Lys Tyr Val Glu Gln Gln Tyr Gly Gln Pro Ser Ser Lys
                360                 365                 370 gct aac atc tta ttg gga gtc ata acc ata cct att ttt gca agt gga   1266
Ala Asn Ile Leu Leu Gly Val Ile Thr Ile Pro Ile Phe Ala Ser Gly
375                 380                 385 atg ttt tta gga gga tat atc att aaa aaa ttc aaa ctg aac acc gtt   1314
Met Phe Leu Gly Gly Tyr Ile Ile Lys Lys Phe Lys Leu Asn Thr Val
390                 395                 400                 405 gga att gcc aaa ttc tca tgt ttt act gct gtg atg tca ttg tcc ttt   1362
Gly Ile Ala Lys Phe Ser Cys Phe Thr Ala Val Met Ser Leu Ser Phe
                410                 415                 420 tac cta tta tat ttt ttc ata ctc tgt gaa aac aaa tca gtt gcc gga   1410
Tyr Leu Leu Tyr Phe Phe Ile Leu Cys Glu Asn Lys Ser Val Ala Gly
            425                 430                 435 cta acc atg acc tat gat gga aat aat cca gtg aca tct cat aga gat   1458
Leu Thr Met Thr Tyr Asp Gly Asn Asn Pro Val Thr Ser His Arg Asp
                440                 445                 450 gta cca ctt tct tat tgc aac tca gac tgc aat tgt gat gaa agt caa   1506
Val Pro Leu Ser Tyr Cys Asn Ser Asp Cys Asn Cys Asp Glu Ser Gln
455                 460                 465 tgg gaa cca gtc tgt gga aac aat gga ata act tac atc tca ccc tgt   1554
Trp Glu Pro Val Cys Gly Asn Asn Gly Ile Thr Tyr Ile Ser Pro Cys
470                 475                 480                 485 cta gca ggt tgc aaa tct tca agt ggc aat aaa aag cct ata gtg ttt   1602
Leu Ala Gly Cys Lys Ser Ser Ser Gly Asn Lys Lys Pro Ile Val Phe
                490                 495                 500 tac aac tgc agt tgt ttg gaa gta act ggt ctc cag aac aga aat tac   1650
Tyr Asn Cys Ser Cys Leu Glu Val Thr Gly Leu Gln Asn Arg Asn Tyr
```

```
                    505                 510                 515
tca gcc cat ttg ggt gaa tgc cca aga gat gat gct tgt aca agg aaa        1698
Ser Ala His Leu Gly Glu Cys Pro Arg Asp Asp Ala Cys Thr Arg Lys
        520                 525                 530 ttt tac ttt ttt gtt gca ata caa gtc ttg aat tta ttt ttc tct gca        1746
Phe Tyr Phe Phe Val Ala Ile Gln Val Leu Asn Leu Phe Phe Ser Ala
    535                 540                 545 ctt gga ggc acc tca cat gtc atg ctg att gtt aaa att gtt caa cct        1794
Leu Gly Gly Thr Ser His Val Met Leu Ile Val Lys Ile Val Gln Pro
550                 555                 560                 565 gaa ttg aaa tca ctt gca ctg ggt ttc cac tca atg gtt ata cga gca        1842
Glu Leu Lys Ser Leu Ala Leu Gly Phe His Ser Met Val Ile Arg Ala
                570                 575                 580 cta gga gga att cta gct cca ata tat ttt ggg gct ctg att gat aca        1890
Leu Gly Gly Ile Leu Ala Pro Ile Tyr Phe Gly Ala Leu Ile Asp Thr
            585                 590                 595 acg tgt ata aag tgg tcc acc aac aac tgt ggc aca cgt ggg tca tgt        1938
Thr Cys Ile Lys Trp Ser Thr Asn Asn Cys Gly Thr Arg Gly Ser Cys
        600                 605                 610 agg aca tat aat tcc aca tca ttt tca agg gtc tac ttg ggc ttg tct        1986
Arg Thr Tyr Asn Ser Thr Ser Phe Ser Arg Val Tyr Leu Gly Leu Ser
    615                 620                 625 tca atg tta aga gtc tca tca ctt gtt tta tat att ata tta att tat        2034
Ser Met Leu Arg Val Ser Ser Leu Val Leu Tyr Ile Ile Leu Ile Tyr
630                 635                 640                 645 gcc atg aag aaa aaa tat caa gag aaa gat atc aat gca tca gaa aat        2082
Ala Met Lys Lys Lys Tyr Gln Glu Lys Asp Ile Asn Ala Ser Glu Asn
                650                 655                 660 gga agt gtc atg gat gaa gca aac tta gaa tcc tta aat aaa aat aaa        2130
Gly Ser Val Met Asp Glu Ala Asn Leu Glu Ser Leu Asn Lys Asn Lys
            665                 670                 675 cat ttt gtc cct tct gct ggg gca gat agt gaa aca cat tgt                2172
His Phe Val Pro Ser Ala Gly Ala Asp Ser Glu Thr His Cys
        680                 685                 690 taagggaga aaaaaagcca cttctgcttc tgtgtttcca aacagcattg cattgattca        2232
gtaagatgtt attttgagg agttcctggt cctttcacta agaatttcca catcttttat        2292
ggtggaagta taaataagcc tatgaactta taataaaaca aactgtaggt agaaaaaatg      2352
agagtactca ttgtacatta tagctacata tttgtggtta aggttagact atatgatcca      2412
tacaaattaa agtgagagac atggttactg tgtaataaaa                            2452

<210> SEQ ID NO 4
<211> LENGTH: 691
<212> TYPE: PRT
<213> ORGANISM: Homo sapiens

<400> SEQUENCE: 4

Met Asp Gln Asn Gln His Leu Asn Lys Thr Ala Glu Ala Gln Pro Ser
 1               5                  10                  15

Glu Asn Lys Lys Thr Arg Tyr Cys Asn Gly Leu Lys Met Phe Leu Ala
            20                  25                  30

Ala Leu Ser Leu Ser Phe Ile Ala Lys Thr Leu Gly Ala Ile Ile Met
        35                  40                  45

Lys Ser Ser Ile Ile His Ile Glu Arg Arg Phe Glu Ile Ser Ser Ser
    50                  55                  60

Leu Val Gly Phe Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
```

-continued

```
                85                  90                  95
Ile Gly Ile Gly Cys Phe Ile Met Gly Ile Gly Val Leu Thr Ala
            100                 105                 110
Leu Pro His Phe Phe Met Gly Tyr Tyr Arg Tyr Ser Lys Glu Thr Asn
            115                 120                 125
Ile Asn Ser Ser Glu Asn Ser Thr Ser Thr Leu Ser Thr Cys Leu Ile
130                 135                 140
Asn Gln Ile Leu Ser Leu Asn Arg Ala Ser Pro Glu Ile Val Gly Lys
145                 150                 155                 160
Gly Cys Leu Lys Glu Ser Gly Ser Tyr Met Trp Ile Tyr Val Phe Met
                165                 170                 175
Gly Asn Met Leu Arg Gly Ile Gly Glu Thr Pro Ile Val Pro Leu Gly
                180                 185                 190
Leu Ser Tyr Ile Asp Asp Phe Ala Lys Glu Gly His Ser Ser Leu Tyr
                195                 200                 205
Leu Gly Ile Leu Asn Ala Ile Ala Met Ile Gly Pro Ile Ile Gly Phe
            210                 215                 220
Thr Leu Gly Ser Leu Phe Ser Lys Met Tyr Val Asp Ile Gly Tyr Val
225                 230                 235                 240
Asp Leu Ser Thr Ile Arg Ile Thr Pro Thr Asp Ser Arg Trp Val Gly
                245                 250                 255
Ala Trp Trp Leu Asn Phe Leu Val Ser Gly Leu Phe Ser Ile Ile Ser
                260                 265                 270
Ser Ile Pro Phe Phe Phe Leu Pro Gln Thr Pro Asn Lys Pro Gln Lys
                275                 280                 285
Glu Arg Lys Ala Ser Leu Ser Leu His Val Leu Glu Thr Asn Asp Glu
            290                 295                 300
Lys Asp Gln Thr Ala Asn Leu Thr Asn Gln Gly Lys Asn Ile Thr Lys
305                 310                 315                 320
Asn Val Thr Gly Phe Phe Gln Ser Phe Lys Ser Ile Leu Thr Asn Pro
                325                 330                 335
Leu Tyr Val Met Phe Val Leu Leu Thr Leu Leu Gln Val Ser Ser Tyr
                340                 345                 350
Ile Gly Ala Phe Thr Tyr Val Phe Lys Tyr Val Glu Gln Gln Tyr Gly
            355                 360                 365
Gln Pro Ser Ser Lys Ala Asn Ile Leu Leu Gly Val Ile Thr Ile Pro
            370                 375                 380
Ile Phe Ala Ser Gly Met Phe Leu Gly Gly Tyr Ile Ile Lys Lys Phe
385                 390                 395                 400
Lys Leu Asn Thr Val Gly Ile Ala Lys Phe Ser Cys Phe Thr Ala Val
                405                 410                 415
Met Ser Leu Ser Phe Tyr Leu Leu Tyr Phe Phe Ile Leu Cys Glu Asn
                420                 425                 430
Lys Ser Val Ala Gly Leu Thr Met Thr Tyr Asp Gly Asn Asn Pro Val
            435                 440                 445
Thr Ser His Arg Asp Val Pro Leu Ser Tyr Cys Asn Ser Asp Cys Asn
450                 455                 460
Cys Asp Glu Ser Gln Trp Glu Pro Val Cys Gly Asn Asn Gly Ile Thr
465                 470                 475                 480
Tyr Ile Ser Pro Cys Leu Ala Gly Cys Lys Ser Ser Gly Asn Lys
                485                 490                 495
Lys Pro Ile Val Phe Tyr Asn Cys Ser Cys Leu Glu Val Thr Gly Leu
                500                 505                 510
```

-continued

```
        Gln Asn Arg Asn Tyr Ser Ala His Leu Gly Glu Cys Pro Arg Asp Asp
            515                 520                 525

Ala Cys Thr Arg Lys Phe Tyr Phe Val Ala Ile Gln Val Leu Asn
        530                 535                 540

Leu Phe Phe Ser Ala Leu Gly Gly Thr Ser His Val Met Leu Ile Val
        545                 550                 555                 560

Lys Ile Val Gln Pro Glu Leu Lys Ser Leu Ala Leu Gly Phe His Ser
                        565                 570                 575

Met Val Ile Arg Ala Leu Gly Gly Ile Leu Ala Pro Ile Tyr Phe Gly
                            580                 585                 590

Ala Leu Ile Asp Thr Thr Cys Ile Lys Trp Ser Thr Asn Asn Cys Gly
                        595                 600                 605

Thr Arg Gly Ser Cys Arg Thr Tyr Asn Ser Thr Ser Phe Ser Arg Val
        610                 615                 620

Tyr Leu Gly Leu Ser Ser Met Leu Arg Val Ser Ser Leu Val Leu Tyr
        625                 630                 635                 640

Ile Ile Leu Ile Tyr Ala Met Lys Lys Tyr Gln Glu Lys Asp Ile
                        645                 650                 655

Asn Ala Ser Glu Asn Gly Ser Val Met Asp Glu Ala Asn Leu Glu Ser
                    660                 665                 670

Leu Asn Lys Asn Lys His Phe Val Pro Ser Ala Gly Ala Asp Ser Glu
                    675                 680                 685

Thr His Cys
                    690

<210> SEQ ID NO 5
<211> LENGTH: 2547
<212> TYPE: DNA
<213> ORGANISM: Homo sapiens
<220> FEATURE:
<221> NAME/KEY: CDS
<222> LOCATION: (1)..(2130)

<400> SEQUENCE: 5 atg cag ggg aag aag ccg ggt ggt tcg tcg ggc ggc ggc cgg agc ggc      48
Met Gln Gly Lys Lys Pro Gly Gly Ser Ser Gly Gly Gly Arg Ser Gly
1               5                   10                  15 gag ctg cag ggg gac gag gcg cag agg aac aag aaa aag aag aag          96
Glu Leu Gln Gly Asp Glu Ala Gln Arg Asn Lys Lys Lys Lys Lys
            20                  25                  30 gtg tcc tgc ttt tcc aac atc aag atc ttc ctg gtg tcc gag tgc gcc    144
Val Ser Cys Phe Ser Asn Ile Lys Ile Phe Leu Val Ser Glu Cys Ala
        35                  40                  45 ctg atg ctg gcg cag ggc acg gtg ggc gcc tac ctg gtg agc gtc ctg    192
Leu Met Leu Ala Gln Gly Thr Val Gly Ala Tyr Leu Val Ser Val Leu
    50                  55                  60 acc acc ctg gag cgt agg ttc aac ctg cag agc gct gac gtg ggt gtg    240
Thr Thr Leu Glu Arg Arg Phe Asn Leu Gln Ser Ala Asp Val Gly Val
65                  70                  75                  80 atc gct agc agc ttc gag atc ggg aac ctg gcg ctc atc ctc ttc gtg    288
Ile Ala Ser Ser Phe Glu Ile Gly Asn Leu Ala Leu Ile Leu Phe Val
                85                  90                  95 agc tac ttc ggg gca cgc ggg cac cgg ccg cgc ctg atc ggc tgc ggc    336
Ser Tyr Phe Gly Ala Arg Gly His Arg Pro Arg Leu Ile Gly Cys Gly
            100                 105                 110 ggc atc gtc atg gcg ctg ggc gcg ctg ctg tcg gcg ctg ccc gag ttc    384
Gly Ile Val Met Ala Leu Gly Ala Leu Leu Ser Ala Leu Pro Glu Phe
        115                 120                 125 ctg acc cac cag tac aag tac gag gcg ggc gag atc cgc tgg ggc gcc    432
```

-continued

| | | |
|---|---|---|
| Leu Thr His Gln Tyr Lys Tyr Glu Ala Gly Glu Ile Arg Trp Gly Ala<br>130     135     140 | | |
| gag ggc cgc gac gtc tgc gca gcc aac ggc tcg ggc ggc gac gag ggg<br>Glu Gly Arg Asp Val Cys Ala Ala Asn Gly Ser Gly Gly Asp Glu Gly<br>145     150     155     160 | | 480 |
| ccc gac ccc gac ctc atc tgc cgc aac cgg acg gct acc aac atg atg<br>Pro Asp Pro Asp Leu Ile Cys Arg Asn Arg Thr Ala Thr Asn Met Met<br>      165     170     175 | | 528 |
| tac ttg ctc ctc att ggg gcc cag gtc ctc ctg ggc atc ggt gct acc<br>Tyr Leu Leu Leu Ile Gly Ala Gln Val Leu Leu Gly Ile Gly Ala Thr<br>    180     185     190 | | 576 |
| cct gtg cag ccc ctg ggc gtc tcc tac tac gac gac cac gtg cgg agg<br>Pro Val Gln Pro Leu Gly Val Ser Tyr Tyr Asp Asp His Val Arg Arg<br>195     200     205 | | 624 |
| aag gac tcc tcg ctc tat ata gga atc ctg ttc acg atg ctg gta ttt<br>Lys Asp Ser Ser Leu Tyr Ile Gly Ile Leu Phe Thr Met Leu Val Phe<br>210     215     220 | | 672 |
| gga cca gcc tgc ggg ttt atc ctg ggc tct ttc tgt acc aaa atc tac<br>Gly Pro Ala Cys Gly Phe Ile Leu Gly Ser Phe Cys Thr Lys Ile Tyr<br>225     230     235     240 | | 720 |
| gtg gat gcg gtc ttc att gac aca agt aac ctg gac atc act ccg gac<br>Val Asp Ala Val Phe Ile Asp Thr Ser Asn Leu Asp Ile Thr Pro Asp<br>      245     250     255 | | 768 |
| gac ccc cgc tgg atc gga gcc tgg tgg ggt ggc ttt ctg ctc tgc ggt<br>Asp Pro Arg Trp Ile Gly Ala Trp Trp Gly Gly Phe Leu Leu Cys Gly<br>    260     265     270 | | 816 |
| gcc tta ctc ttc ttc tct tcc ctc ttg atg ttt ggg ttt cca cag tcc<br>Ala Leu Leu Phe Phe Ser Ser Leu Leu Met Phe Gly Phe Pro Gln Ser<br>275     280     285 | | 864 |
| ctg ccc ccg cac tca gac ccc gcc atg gaa agc gag cag gcc atg ctc<br>Leu Pro Pro His Ser Asp Pro Ala Met Glu Ser Glu Gln Ala Met Leu<br>290     295     300 | | 912 |
| tcc gaa aga gaa tac gag aga ccc aag ccc agc aac ggg gtc ctg agg<br>Ser Glu Arg Glu Tyr Glu Arg Pro Lys Pro Ser Asn Gly Val Leu Arg<br>305     310     315     320 | | 960 |
| cac ccc ctg gag cca gac agc agt gcc tcc tgt ttc cag cag ctg aga<br>His Pro Leu Glu Pro Asp Ser Ser Ala Ser Cys Phe Gln Gln Leu Arg<br>      325     330     335 | | 1008 |
| gtg atc ccg aag gtc acc aag cac ctg ctc tca aac cct gtg ttc acc<br>Val Ile Pro Lys Val Thr Lys His Leu Leu Ser Asn Pro Val Phe Thr<br>    340     345     350 | | 1056 |
| tgc atc atc ctg gcc gcc tgc atg gag att gca gtg gtg gct ggc ttc<br>Cys Ile Ile Leu Ala Ala Cys Met Glu Ile Ala Val Val Ala Gly Phe<br>355     360     365 | | 1104 |
| gct gcc ttt ttg ggg aag tac ctg gag cag cag ttt aac ctc acc acc<br>Ala Ala Phe Leu Gly Lys Tyr Leu Glu Gln Gln Phe Asn Leu Thr Thr<br>370     375     380 | | 1152 |
| tct tct gcc aac cag ctg ctt ggg atg act gcg atc ccg tgt gct tgt<br>Ser Ser Ala Asn Gln Leu Leu Gly Met Thr Ala Ile Pro Cys Ala Cys<br>385     390     395     400 | | 1200 |
| ctg ggt atc ttc ctg gga ggt ctt ttg gtg aag aag ctc agc ctg tct<br>Leu Gly Ile Phe Leu Gly Gly Leu Leu Val Lys Lys Leu Ser Leu Ser<br>      405     410     415 | | 1248 |
| gcc ctg ggg gcc att cgg atg gcc atg ctc gtc aac ctg gtg tcc act<br>Ala Leu Gly Ala Ile Arg Met Ala Met Leu Val Asn Leu Val Ser Thr<br>    420     425     430 | | 1296 |
| gct tgc tac gtc tcc ttc ctc ttc ctg ggc tgc gac act ggc cct gtg<br>Ala Cys Tyr Val Ser Phe Leu Phe Leu Gly Cys Asp Thr Gly Pro Val<br>435     440     445 | | 1344 |
| gct ggg gtt act gtt ccc tat gga aac agc aca gca cct ggc tca gcc | | 1392 |

-continued

```
Ala Gly Val Thr Val Pro Tyr Gly Asn Ser Thr Ala Pro Gly Ser Ala
         450                 455                 460 ctg gac ccc tac tcg ccc tgc aat aat aac tgt gaa tgc caa acc gat    1440
Leu Asp Pro Tyr Ser Pro Cys Asn Asn Asn Cys Glu Cys Gln Thr Asp
465                 470                 475                 480 tcc ttc act cca gtg tgt ggg gca gat ggc atc acc tac ctg tct gcc    1488
Ser Phe Thr Pro Val Cys Gly Ala Asp Gly Ile Thr Tyr Leu Ser Ala
                485                 490                 495 tgc ttt gct ggc tgc aac agc acg aat ctc acg ggc tgt gcg tgc ctc    1536
Cys Phe Ala Gly Cys Asn Ser Thr Asn Leu Thr Gly Cys Ala Cys Leu
                500                 505                 510 acc acc gtc cct gct gag aac gca acc gtg gtt cct gga aaa tgc ccc    1584
Thr Thr Val Pro Ala Glu Asn Ala Thr Val Val Pro Gly Lys Cys Pro
            515                 520                 525 agt cct ggg tgc caa gag gcc ttc ctc act ttc ctc tgt gtg atg tgt    1632
Ser Pro Gly Cys Gln Glu Ala Phe Leu Thr Phe Leu Cys Val Met Cys
        530                 535                 540 atc tgc agc ctg atc ggt gcc atg gca cag aca ccc tca gtc atc atc    1680
Ile Cys Ser Leu Ile Gly Ala Met Ala Gln Thr Pro Ser Val Ile Ile
545                 550                 555                 560 ctc atc agg aca gtc agc cct gaa ctc aag tct tac gct ttg gga gtt    1728
Leu Ile Arg Thr Val Ser Pro Glu Leu Lys Ser Tyr Ala Leu Gly Val
                565                 570                 575 ctt ttt ctc ctc ctt cgt ttg ttg ggc ttc atc cct cca ccc ctc atc    1776
Leu Phe Leu Leu Leu Arg Leu Leu Gly Phe Ile Pro Pro Pro Leu Ile
                580                 585                 590 ttc ggg gct ggc atc gac tcc acc tgc ctg ttc tgg agc acg ttc tgt    1824
Phe Gly Ala Gly Ile Asp Ser Thr Cys Leu Phe Trp Ser Thr Phe Cys
                595                 600                 605 ggg gag caa ggc gcc tgc gtc ctc tac gac aat gtg gtc tac cga tac    1872
Gly Glu Gln Gly Ala Cys Val Leu Tyr Asp Asn Val Val Tyr Arg Tyr
610                 615                 620 ctg tat gtc agc atc gcc atc gcg ctc aaa tcc ttc gcc ttc atc ctg    1920
Leu Tyr Val Ser Ile Ala Ile Ala Leu Lys Ser Phe Ala Phe Ile Leu
625                 630                 635                 640 tac acc acg acg tgg cag tgc ctg agg aaa aac tat aaa cgc tac atc    1968
Tyr Thr Thr Thr Trp Gln Cys Leu Arg Lys Asn Tyr Lys Arg Tyr Ile
                645                 650                 655 aaa aac cac gag ggc ggg ctg agc acc agt gag ttc ttt gcc tct act    2016
Lys Asn His Glu Gly Gly Leu Ser Thr Ser Glu Phe Phe Ala Ser Thr
                660                 665                 670 ctg acc cta gac aac ctg ggg agg gac cct gtg ccc gca aac cag aca    2064
Leu Thr Leu Asp Asn Leu Gly Arg Asp Pro Val Pro Ala Asn Gln Thr
                675                 680                 685 cat agg aca aag ttt atc tat aac ctg gaa gac cat gag tgg tgt gaa    2112
His Arg Thr Lys Phe Ile Tyr Asn Leu Glu Asp His Glu Trp Cys Glu
        690                 695                 700 aac atg gag tcc gtt tta tagtgactaa aggagggctg aactctgtat           2160
Asn Met Glu Ser Val Leu
705                 710 tagtaatcca agggtcattt ttttcttaaa aaaagaaaaa aaggttccaa aaaaaaccaa  2220
aactcagtac acacacacag gcacagatgc acacacacgc agacagacac accgactttg  2280 tccttttttct cagcatcaga gccagacagg attcagaata aggagagaat gacatcgtgc 2340
ggcagggtcc tggaggccac tcgcgcggct gggccacaga gtctactttg aaggcacctc  2400
atggttttca ggatgctgac agctgcaagc aacaggcact gccaaattca gggaacagtg  2460
gtggccagct tggaggatgg acatttctgg atacacatac acatacaaaa cagaaaacat  2520
tttttaaaag aagtttccta aaataaa                                     2547
```

<210> SEQ ID NO 6
<211> LENGTH: 710
<212> TYPE: PRT
<213> ORGANISM: Homo sapiens

<400> SEQUENCE: 6

```
Met Gln Gly Lys Lys Pro Gly Ser Gly Gly Arg Ser Gly
 1               5                  10                  15

Glu Leu Gln Gly Asp Glu Ala Gln Arg Asn Lys Lys Lys Lys
                20                  25                  30

Val Ser Cys Phe Ser Asn Ile Lys Ile Phe Leu Val Ser Glu Cys Ala
                35                  40                  45

Leu Met Leu Ala Gln Gly Thr Val Gly Ala Tyr Leu Val Ser Val Leu
    50                  55                  60

Thr Thr Leu Glu Arg Arg Phe Asn Leu Gln Ser Ala Asp Val Gly Val
 65                  70                  75                  80

Ile Ala Ser Ser Phe Glu Ile Gly Asn Leu Ala Leu Ile Leu Phe Val
                85                  90                  95

Ser Tyr Phe Gly Ala Arg Gly His Arg Pro Arg Leu Ile Gly Cys Gly
                100                 105                 110

Gly Ile Val Met Ala Leu Gly Ala Leu Leu Ser Ala Leu Pro Glu Phe
            115                 120                 125

Leu Thr His Gln Tyr Lys Tyr Glu Ala Gly Glu Ile Arg Trp Gly Ala
    130                 135                 140

Glu Gly Arg Asp Val Cys Ala Ala Asn Gly Ser Gly Gly Asp Glu Gly
145                 150                 155                 160

Pro Asp Pro Asp Leu Ile Cys Arg Asn Arg Thr Ala Thr Asn Met Met
                165                 170                 175

Tyr Leu Leu Leu Ile Gly Ala Gln Val Leu Leu Gly Ile Gly Ala Thr
                180                 185                 190

Pro Val Gln Pro Leu Gly Val Ser Tyr Tyr Asp Asp His Val Arg Arg
            195                 200                 205

Lys Asp Ser Ser Leu Tyr Ile Gly Ile Leu Phe Thr Met Leu Val Phe
210                 215                 220

Gly Pro Ala Cys Gly Phe Ile Leu Gly Ser Phe Cys Thr Lys Ile Tyr
225                 230                 235                 240

Val Asp Ala Val Phe Ile Asp Thr Ser Asn Leu Asp Ile Thr Pro Asp
                245                 250                 255

Asp Pro Arg Trp Ile Gly Ala Trp Trp Gly Gly Phe Leu Leu Cys Gly
                260                 265                 270

Ala Leu Leu Phe Phe Ser Ser Leu Leu Met Phe Gly Phe Pro Gln Ser
            275                 280                 285

Leu Pro Pro His Ser Asp Pro Ala Met Glu Ser Glu Gln Ala Met Leu
    290                 295                 300

Ser Glu Arg Glu Tyr Glu Arg Pro Lys Pro Ser Asn Gly Val Leu Arg
305                 310                 315                 320

His Pro Leu Glu Pro Asp Ser Ser Ala Ser Cys Phe Gln Gln Leu Arg
                325                 330                 335

Val Ile Pro Lys Val Thr Lys His Leu Leu Ser Asn Pro Val Phe Thr
                340                 345                 350

Cys Ile Ile Leu Ala Ala Cys Met Glu Ile Ala Val Val Ala Gly Phe
            355                 360                 365

Ala Ala Phe Leu Gly Lys Tyr Leu Glu Gln Gln Phe Asn Leu Thr Thr
    370                 375                 380
```

```
Ser Ser Ala Asn Gln Leu Leu Gly Met Thr Ala Ile Pro Cys Ala Cys
385                 390                 395                 400

Leu Gly Ile Phe Leu Gly Gly Leu Leu Val Lys Lys Leu Ser Leu Ser
            405                 410                 415

Ala Leu Gly Ala Ile Arg Met Ala Met Leu Val Asn Leu Val Ser Thr
        420                 425                 430

Ala Cys Tyr Val Ser Phe Leu Phe Leu Gly Cys Asp Thr Gly Pro Val
    435                 440                 445

Ala Gly Val Thr Val Pro Tyr Gly Asn Ser Thr Ala Pro Gly Ser Ala
450                 455                 460

Leu Asp Pro Tyr Ser Pro Cys Asn Asn Asn Cys Glu Cys Gln Thr Asp
465                 470                 475                 480

Ser Phe Thr Pro Val Cys Gly Ala Asp Gly Ile Thr Tyr Leu Ser Ala
                485                 490                 495

Cys Phe Ala Gly Cys Asn Ser Thr Asn Leu Thr Gly Cys Ala Cys Leu
            500                 505                 510

Thr Thr Val Pro Ala Glu Asn Ala Thr Val Val Pro Gly Lys Cys Pro
        515                 520                 525

Ser Pro Gly Cys Gln Glu Ala Phe Leu Thr Phe Leu Cys Val Met Cys
    530                 535                 540

Ile Cys Ser Leu Ile Gly Ala Met Ala Gln Thr Pro Ser Val Ile Ile
545                 550                 555                 560

Leu Ile Arg Thr Val Ser Pro Glu Leu Lys Ser Tyr Ala Leu Gly Val
                565                 570                 575

Leu Phe Leu Leu Leu Arg Leu Leu Gly Phe Ile Pro Pro Leu Ile
            580                 585                 590

Phe Gly Ala Gly Ile Asp Ser Thr Cys Leu Phe Trp Ser Thr Phe Cys
        595                 600                 605

Gly Glu Gln Gly Ala Cys Val Leu Tyr Asp Asn Val Val Tyr Arg Tyr
    610                 615                 620

Leu Tyr Val Ser Ile Ala Ile Ala Leu Lys Ser Phe Ala Phe Ile Leu
625                 630                 635                 640

Tyr Thr Thr Thr Trp Gln Cys Leu Arg Lys Asn Tyr Lys Arg Tyr Ile
                645                 650                 655

Lys Asn His Glu Gly Gly Leu Ser Thr Ser Glu Phe Phe Ala Ser Thr
            660                 665                 670

Leu Thr Leu Asp Asn Leu Gly Arg Asp Pro Val Pro Ala Asn Gln Thr
        675                 680                 685

His Arg Thr Lys Phe Ile Tyr Asn Leu Glu Asp His Glu Trp Cys Glu
690                 695                 700

Asn Met Glu Ser Val Leu
705             710

<210> SEQ ID NO 7
<211> LENGTH: 2660
<212> TYPE: DNA
<213> ORGANISM: Homo sapiens
<220> FEATURE:
<221> NAME/KEY: CDS
<222> LOCATION: (92)..(2257)

<400> SEQUENCE: 7
accagcccct cggataccac ttggccactc ccgctgaggc cactcccact gcgtggctga        60
agcctcgagg tcaccaggcg gaggcgcgga g atg ccc ctg cat cag ctg ggg          112
                                  Met Pro Leu His Gln Leu Gly
                                    1               5
```

```
gac aag ccg ctc acc ttc ccc agc ccc aac tca gcc atg gaa aac ggg      160
Asp Lys Pro Leu Thr Phe Pro Ser Pro Asn Ser Ala Met Glu Asn Gly
         10                  15                  20 ctt gac cac acc cca ccc agc agg agg gca tcc ccg ggc aca ccc ctg      208
Leu Asp His Thr Pro Pro Ser Arg Arg Ala Ser Pro Gly Thr Pro Leu
     25                  30                  35 agc ccc ggc tcc ctc cgc tcc gct gcc cat agc ccc ctg gac acc agc      256
Ser Pro Gly Ser Leu Arg Ser Ala Ala His Ser Pro Leu Asp Thr Ser
 40                  45                  50                  55 aag cag ccc ctc tgc cag ctc tgg gcc gag aag cat ggc gcc cgg ggg      304
Lys Gln Pro Leu Cys Gln Leu Trp Ala Glu Lys His Gly Ala Arg Gly
                 60                  65                  70 acc cat gag gtg cgg tac gtc tcg gcc ggg cag agc gtg gcg tgc ggc      352
Thr His Glu Val Arg Tyr Val Ser Ala Gly Gln Ser Val Ala Cys Gly
             75                  80                  85 tgg tgg gcc ttc gca ccg ccg tgc ctg cag gtc ctc aac acg ccc aag      400
Trp Trp Ala Phe Ala Pro Pro Cys Leu Gln Val Leu Asn Thr Pro Lys
         90                  95                 100 ggc atc ctg ttc ttc ctg tgt gcg gcc gca ttc ctg cag ggg atg act      448
Gly Ile Leu Phe Phe Leu Cys Ala Ala Ala Phe Leu Gln Gly Met Thr
105                 110                 115 gtg aat ggc ttc atc aac aca gtc atc acc tcc ctg gag cgc cgc tat      496
Val Asn Gly Phe Ile Asn Thr Val Ile Thr Ser Leu Glu Arg Arg Tyr
120                 125                 130                 135 gac ctg cac agc tac cag agc ggg ctc atc gcc agc tcc tac gac att      544
Asp Leu His Ser Tyr Gln Ser Gly Leu Ile Ala Ser Ser Tyr Asp Ile
                140                 145                 150 gcc gcc tgc ctc tgc ctc acc ttc gtc agc tac ttc ggg ggc tca ggg      592
Ala Ala Cys Leu Cys Leu Thr Phe Val Ser Tyr Phe Gly Gly Ser Gly
            155                 160                 165 cac aag ccg cgc tgg ctg ggc tgg ggc gtg ctg ctt atg ggc acg ggg      640
His Lys Pro Arg Trp Leu Gly Trp Gly Val Leu Leu Met Gly Thr Gly
        170                 175                 180 tcg ctg gtg ttc gcg ctg ccc cac ttc acg gct ggc cgc tat gag gtg      688
Ser Leu Val Phe Ala Leu Pro His Phe Thr Ala Gly Arg Tyr Glu Val
185                 190                 195 gag ttg gac gcg ggt gtc agg acg tgc cct gcc aac ccc ggc gcg gtg      736
Glu Leu Asp Ala Gly Val Arg Thr Cys Pro Ala Asn Pro Gly Ala Val
200                 205                 210                 215 tgt gcg gac agc acc tcg ggc ctg tcc cgc tac cag ctg gtc ttc atg      784
Cys Ala Asp Ser Thr Ser Gly Leu Ser Arg Tyr Gln Leu Val Phe Met
                220                 225                 230 ctg ggc cag ttc ctg cat ggc gtg ggt gcc aca ccc ctc tac acg ctg      832
Leu Gly Gln Phe Leu His Gly Val Gly Ala Thr Pro Leu Tyr Thr Leu
            235                 240                 245 ggc gtc acc tac ctg gat gag aac gtc aag tcc agc tgc tcg ccc gtc      880
Gly Val Thr Tyr Leu Asp Glu Asn Val Lys Ser Ser Cys Ser Pro Val
        250                 255                 260 tac att gcc atc ttc tac aca gcg gcc atc ctg ggc cca gct gcc ggc      928
Tyr Ile Ala Ile Phe Tyr Thr Ala Ala Ile Leu Gly Pro Ala Ala Gly
265                 270                 275 tac ctg att gga ggt gcc ctg ctg aat atc tac acg gaa atg ggc cga      976
Tyr Leu Ile Gly Gly Ala Leu Leu Asn Ile Tyr Thr Glu Met Gly Arg
280                 285                 290                 295 cgg acg gag ctg acc acc gag agc cca ctg tgg gtc ggc gcc tgg tgg     1024
Arg Thr Glu Leu Thr Thr Glu Ser Pro Leu Trp Val Gly Ala Trp Trp
                300                 305                 310 gtc ggc ttc ctg ggc tct ggg gcc gct gct ttc ttc acc gcc gtt ccc     1072
Val Gly Phe Leu Gly Ser Gly Ala Ala Ala Phe Phe Thr Ala Val Pro
            315                 320                 325
```

```
atc ctt ggt tac cct cgg cag ctg cca ggc tcc cag cgc tac gcg gtc      1120
Ile Leu Gly Tyr Pro Arg Gln Leu Pro Gly Ser Gln Arg Tyr Ala Val
        330                 335                 340 atg aga gcg gcg gaa atg cac cag ttg aag gac agc agc cgt ggg gag      1168
Met Arg Ala Ala Glu Met His Gln Leu Lys Asp Ser Ser Arg Gly Glu
345                 350                 355 gcg agc aac ccg gac ttt ggg aaa acc atc aga gac ctg cct ctc tcc      1216
Ala Ser Asn Pro Asp Phe Gly Lys Thr Ile Arg Asp Leu Pro Leu Ser
360                 365                 370                 375 atc tgg ctc ctg ctg aag aac ccc acg ttc atc ctg ctc tgc ctg gcc      1264
Ile Trp Leu Leu Leu Lys Asn Pro Thr Phe Ile Leu Leu Cys Leu Ala
            380                 385                 390 ggg gcc acc gag gcc act ctc atc acc ggc atg tcc acg ttc agc ccc      1312
Gly Ala Thr Glu Ala Thr Leu Ile Thr Gly Met Ser Thr Phe Ser Pro
    395                 400                 405 aag ttc ttg gag tcc cag ttc agc ctg agt gcc tca gaa gct gcc acc      1360
Lys Phe Leu Glu Ser Gln Phe Ser Leu Ser Ala Ser Glu Ala Ala Thr
410                 415                 420 ttg ttt ggg tac ctg gtg gtg cca gcg ggt ggt ggc acc ttc ctg           1408
Leu Phe Gly Tyr Leu Val Val Pro Ala Gly Gly Gly Thr Phe Leu
    425                 430                 435 ggc ggc ttc ttt gtg aac aag ctc agg ctc cgg ggc tcc gcg gtc atc      1456
Gly Gly Phe Phe Val Asn Lys Leu Arg Leu Arg Gly Ser Ala Val Ile
440                 445                 450                 455 aag ttc tgc ctg ttc tgc acc gtt gtc agc ctg ctg ggc atc ctc gtc      1504
Lys Phe Cys Leu Phe Cys Thr Val Val Ser Leu Leu Gly Ile Leu Val
            460                 465                 470 ttc tca ctg cac tgc ccc agt gtg ccc atg gcg ggc gtc aca gcc agc      1552
Phe Ser Leu His Cys Pro Ser Val Pro Met Ala Gly Val Thr Ala Ser
    475                 480                 485 tac ggc ggg agc ctc ctg ccc gaa ggc cac ctg aac cta acg gct ccc      1600
Tyr Gly Gly Ser Leu Leu Pro Glu Gly His Leu Asn Leu Thr Ala Pro
490                 495                 500 tgc aac gct gcc tgc agc tgc cag cca gaa cac tac agc cct gtg tgc      1648
Cys Asn Ala Ala Cys Ser Cys Gln Pro Glu His Tyr Ser Pro Val Cys
    505                 510                 515 ggc tcg gac ggc ctc atg tac ttc tca ctg tgc cac gca ggg tgc cct      1696
Gly Ser Asp Gly Leu Met Tyr Phe Ser Leu Cys His Ala Gly Cys Pro
520                 525                 530                 535 gca gcc acg gag acg aat gtg gac ggc cag aag gtg tac cga gac tgt      1744
Ala Ala Thr Glu Thr Asn Val Asp Gly Gln Lys Val Tyr Arg Asp Cys
            540                 545                 550 agc tgt atc cct cag aat ctt tcc tct ggt ttt ggc cat gcc act gca      1792
Ser Cys Ile Pro Gln Asn Leu Ser Ser Gly Phe Gly His Ala Thr Ala
    555                 560                 565 ggg aaa tgc act tca act tgt cag aga aag ccc ctc ctt ctg gtt ttc      1840
Gly Lys Cys Thr Ser Thr Cys Gln Arg Lys Pro Leu Leu Leu Val Phe
570                 575                 580 ata ttc gtt gta att ttc ttt aca ttc ctc agc agc att cct gca cta      1888
Ile Phe Val Val Ile Phe Phe Thr Phe Leu Ser Ser Ile Pro Ala Leu
    585                 590                 595 acg gca act cta cga tgt gtc cgt gac cct cag aga tcc ttt gcc ctg      1936
Thr Ala Thr Leu Arg Cys Val Arg Asp Pro Gln Arg Ser Phe Ala Leu
600                 605                 610                 615 gga atc cag tgg att gta gtt aga ata cta ggg ggc atc ccg ggg ccc      1984
Gly Ile Gln Trp Ile Val Val Arg Ile Leu Gly Gly Ile Pro Gly Pro
            620                 625                 630 atc gcc ttc ggc tgg gtg atc gac aag gcc tgt ctg ctg tgg cag gac      2032
Ile Ala Phe Gly Trp Val Ile Asp Lys Ala Cys Leu Leu Trp Gln Asp
    635                 640                 645
```

-continued

```
cag tgt ggc cag cag ggc tcc tgc ttg gtg tac cag aat tcg gcc atg    2080
Gln Cys Gly Gln Gln Gly Ser Cys Leu Val Tyr Gln Asn Ser Ala Met
        650                 655                 660 agc cgc tac ata ctc atc atg ggg ctc ctg tac aag gtg ctg ggc gtc    2128
Ser Arg Tyr Ile Leu Ile Met Gly Leu Leu Tyr Lys Val Leu Gly Val
    665                 670                 675 ctc ttc ttt gcc ata gcc tgc ttc tta tac aag ccc ctg tcg gag tct    2176
Leu Phe Phe Ala Ile Ala Cys Phe Leu Tyr Lys Pro Leu Ser Glu Ser
680                 685                 690                 695 tca gat ggc ctg gaa act tgt ctg ccc agc cag tcc tca gcc cct gac    2224
Ser Asp Gly Leu Glu Thr Cys Leu Pro Ser Gln Ser Ser Ala Pro Asp
                700                 705                 710 agt gcc aca gat agc cag ctc cag agc agc gtc tgaccaccgc ccgcgcccac  2277
Ser Ala Thr Asp Ser Gln Leu Gln Ser Ser Val
            715                 720 ccggccacgg cgggcactca gcatttcctg atgacagaac agtgccgttg ggtgatgcaa  2337
tcacacggga acttctattt gacctgcaac cttctactta acctgtggtt taaagtcggc  2397
tgtgacctcc tgtccccaga gctgtacggc cctgcagtgg gtgggaggaa cttgcataaa  2457
tatatattta tggacacaca gtttgcatca gaacgtgttt atagaatgtg ttttataccc  2517
gatcgtgtgt ggtgtgcgtg aggacaaact ccgcaggggc tgtgaatccc actgggaggg  2577
cggtgggcct gcagcccgag gaaggcttgt gtgtcctcag ttaaaactgt gcatatcgaa  2637
atatattttg ttatttaagc ctg                                         2660

<210> SEQ ID NO 8
<211> LENGTH: 722
<212> TYPE: PRT
<213> ORGANISM: Homo sapiens

<400> SEQUENCE: 8

Met Pro Leu His Gln Leu Gly Asp Lys Pro Leu Thr Phe Pro Ser Pro
1               5                   10                  15

Asn Ser Ala Met Glu Asn Gly Leu Asp His Thr Pro Pro Ser Arg Arg
            20                  25                  30

Ala Ser Pro Gly Thr Pro Leu Ser Pro Gly Ser Leu Arg Ser Ala Ala
        35                  40                  45

His Ser Pro Leu Asp Thr Ser Lys Gln Pro Leu Cys Gln Leu Trp Ala
    50                  55                  60

Glu Lys His Gly Ala Arg Gly Thr His Glu Val Arg Tyr Val Ser Ala
65                  70                  75                  80

Gly Gln Ser Val Ala Cys Gly Trp Trp Ala Phe Ala Pro Pro Cys Leu
                85                  90                  95

Gln Val Leu Asn Thr Pro Lys Gly Ile Leu Phe Leu Cys Ala Ala
            100                 105                 110

Ala Phe Leu Gln Gly Met Thr Val Asn Gly Phe Ile Asn Thr Val Ile
        115                 120                 125

Thr Ser Leu Glu Arg Arg Tyr Asp Leu His Ser Tyr Gln Ser Gly Leu
    130                 135                 140

Ile Ala Ser Ser Tyr Asp Ile Ala Ala Cys Leu Cys Leu Thr Phe Val
145                 150                 155                 160

Ser Tyr Phe Gly Ser Gly His Lys Pro Arg Trp Leu Gly Trp Gly
                165                 170                 175

Val Leu Leu Met Gly Thr Gly Ser Leu Val Phe Ala Leu Pro His Phe
            180                 185                 190

Thr Ala Gly Arg Tyr Glu Val Glu Leu Asp Ala Gly Val Arg Thr Cys
```

```
            195                 200                 205
Pro Ala Asn Pro Gly Ala Val Cys Ala Asp Ser Thr Ser Gly Leu Ser
210                 215                 220
Arg Tyr Gln Leu Val Phe Met Leu Gly Gln Phe Leu His Gly Val Gly
225                 230                 235                 240
Ala Thr Pro Leu Tyr Thr Leu Gly Val Thr Tyr Leu Asp Glu Asn Val
            245                 250                 255
Lys Ser Ser Cys Ser Pro Val Tyr Ile Ala Ile Phe Tyr Thr Ala Ala
                260                 265                 270
Ile Leu Gly Pro Ala Ala Gly Tyr Leu Ile Gly Gly Ala Leu Leu Asn
            275                 280                 285
Ile Tyr Thr Glu Met Gly Arg Arg Thr Glu Leu Thr Thr Glu Ser Pro
            290                 295                 300
Leu Trp Val Gly Ala Trp Trp Val Gly Phe Leu Gly Ser Gly Ala Ala
305                 310                 315                 320
Ala Phe Phe Thr Ala Val Pro Ile Leu Gly Tyr Pro Arg Gln Leu Pro
                325                 330                 335
Gly Ser Gln Arg Tyr Ala Val Met Arg Ala Ala Glu Met His Gln Leu
                340                 345                 350
Lys Asp Ser Ser Arg Gly Glu Ala Ser Asn Pro Asp Phe Gly Lys Thr
            355                 360                 365
Ile Arg Asp Leu Pro Leu Ser Ile Trp Leu Leu Lys Asn Pro Thr
            370                 375                 380
Phe Ile Leu Leu Cys Leu Ala Gly Ala Thr Glu Ala Thr Leu Ile Thr
385                 390                 395                 400
Gly Met Ser Thr Phe Ser Pro Lys Phe Leu Glu Ser Gln Phe Ser Leu
                405                 410                 415
Ser Ala Ser Glu Ala Ala Thr Leu Phe Gly Tyr Leu Val Val Pro Ala
                420                 425                 430
Gly Gly Gly Gly Thr Phe Leu Gly Gly Phe Phe Val Asn Lys Leu Arg
            435                 440                 445
Leu Arg Gly Ser Ala Val Ile Lys Phe Cys Leu Phe Cys Thr Val Val
450                 455                 460
Ser Leu Leu Gly Ile Leu Val Phe Ser Leu His Cys Pro Ser Val Pro
465                 470                 475                 480
Met Ala Gly Val Thr Ala Ser Tyr Gly Gly Ser Leu Leu Pro Glu Gly
                485                 490                 495
His Leu Asn Leu Thr Ala Pro Cys Asn Ala Ala Cys Ser Cys Gln Pro
            500                 505                 510
Glu His Tyr Ser Pro Val Cys Gly Ser Asp Gly Leu Met Tyr Phe Ser
            515                 520                 525
Leu Cys His Ala Gly Cys Pro Ala Ala Thr Glu Thr Asn Val Asp Gly
            530                 535                 540
Gln Lys Val Tyr Arg Asp Cys Ser Cys Ile Pro Gln Asn Leu Ser Ser
545                 550                 555                 560
Gly Phe Gly His Ala Thr Ala Gly Lys Cys Thr Ser Thr Cys Gln Arg
                565                 570                 575
Lys Pro Leu Leu Leu Val Phe Ile Phe Val Val Ile Phe Phe Thr Phe
            580                 585                 590
Leu Ser Ser Ile Pro Ala Leu Thr Ala Thr Leu Arg Cys Val Arg Asp
            595                 600                 605
Pro Gln Arg Ser Phe Ala Leu Gly Ile Gln Trp Ile Val Val Arg Ile
610                 615                 620
```

```
Leu Gly Gly Ile Pro Gly Pro Ile Ala Phe Gly Trp Val Ile Asp Lys
625                 630                 635                 640

Ala Cys Leu Leu Trp Gln Asp Gln Cys Gly Gln Gly Ser Cys Leu
            645                 650                 655

Val Tyr Gln Asn Ser Ala Met Ser Arg Tyr Ile Leu Ile Met Gly Leu
            660                 665                 670

Leu Tyr Lys Val Leu Gly Val Leu Phe Phe Ala Ile Ala Cys Phe Leu
        675                 680                 685

Tyr Lys Pro Leu Ser Glu Ser Ser Asp Gly Leu Glu Thr Cys Leu Pro
    690                 695                 700

Ser Gln Ser Ser Ala Pro Asp Ser Ala Thr Asp Ser Gln Leu Gln Ser
705                 710                 715                 720

Ser Val

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 9
gataagcttc tgtgtggccc aagaagaact gac                                33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 10
gataagcttt actgctgtgg ctgctactct tgg                                33

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 11
aagcttccgt caataaaacc aaca                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 12
cttctcttgt tggttttatt gacg                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence
```

```
<400> SEQUENCE: 13
tgtaagttat tccattgttt ccac                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 14
ttggtgcttt tacttatgtc ttca                                          24

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 15
gatggtacca aactgagcat caacaacaaa aac                                33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 16
gatggtaccc atcgagaatc agtaggagtt atc                                33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 17
gatggtacct accctgggat ctctgttttc taa                                33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 18
gatggtaccg tttggaaaca cagaagcaga agt                                33

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 19
```

```
cgccctcgtg gttttttgatg tagc                                        24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 20
gcggtgcctt actcttcttc tctt                                         24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 21
cttttgagca agttcagcct                                              20

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 22
agaggtggct tatgagtatt tctt                                         24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 23
tgtacaaggt gctgggcgtc ctct                                         24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 24
cgatcgggta taaaacacat tcta                                         24

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 25
gataagcttt gcgtggctga agcctcgaag tca                               33
```

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 26
gatggatcca ctggtgcatt tccgccgctc tca                          33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 27
gataagcttt cttcaccgcc gttcccatcc ttg                          33

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 28
gatggatcca ctgttctgtc atcaggaaat gct                          33

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 29
aagaagaggt caagaaggaa aaat                                    24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 30
ggagcatcaa ggaacagtca ggtc                                    24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 31
cgtgcggcca agtgtgttcc ataa                                    24

```
<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 32
gaaggagtag ccccatagcc aatc                                            24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 33
tgtcattgtc cttttaccta ttat                                            24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 34
ctcaaatcct tcgccttcat cctg                                            24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 35
agggtcagag tagaggcaaa gaac                                            24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 36
cacggcgggc actcagcatt tcct                                            24

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 37
tgaaggtcgg agtcaacgga tttggt                                          26

<210> SEQ ID NO 38
<211> LENGTH: 24
```

```
<212> TYPE: DNA
<213> ORGANISM: Artificial Sequence
<220> FEATURE:
<223> OTHER INFORMATION: Description of Artificial Sequence:
      artificially synthesized primer sequence

<400> SEQUENCE: 38
catgtgggcc atgaggtcca ccac                                          24
```